US009155297B2

(12) United States Patent
Anderson et al.

(10) Patent No.: US 9,155,297 B2
(45) Date of Patent: *Oct. 13, 2015

(54) METHODS AND SYSTEMS FOR ASSESSING THE SUITABILITY OF AN ORGAN FOR TRANSPLANT

(71) Applicant: Paragonix Technologies, Inc., Braintree, MA (US)

(72) Inventors: Lisa Maria Anderson, Boston, MA (US); Jared Alden Judson, Medford, MA (US)

(73) Assignee: Paragonix Technologies, Inc., Baintree, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,257

(22) Filed: Jun. 26, 2014

(65) Prior Publication Data

US 2014/0308653 A1 Oct. 16, 2014

Related U.S. Application Data

(63) Continuation of application No. 13/572,332, filed on Aug. 10, 2012, now Pat. No. 8,785,116.

(51) Int. Cl.
*A01N 1/02* (2006.01)
*G01N 33/483* (2006.01)
*G06Q 50/22* (2012.01)
*G06Q 10/08* (2012.01)
*G01N 33/487* (2006.01)

(52) U.S. Cl.
CPC .............. *A01N 1/021* (2013.01); *A01N 1/0247* (2013.01); *G01N 33/483* (2013.01); *G01N 33/487* (2013.01); *G06Q 10/08* (2013.01); *G06Q 50/22* (2013.01)

(58) Field of Classification Search
None
See application file for complete search history.

(56) References Cited

U.S. PATENT DOCUMENTS

| | | |
|---|---|---|
| 3,607,646 A | 9/1971 | de Roissart |
| 4,336,248 A | 6/1982 | Bonhard et al. |
| 4,575,498 A | 3/1986 | Holmes et al. |
| 4,952,409 A | 8/1990 | Bando et al. |
| 5,066,578 A | 11/1991 | Wikman-Coffelt |
| 5,141,847 A | 8/1992 | Sugimachi et al. |
| 5,149,321 A | 9/1992 | Klatz et al. |
| 5,234,405 A | 8/1993 | Klatz et al. |
| RE34,387 E | 9/1993 | Holmes et al. |
| 5,252,537 A | 10/1993 | De Winter-Scailteur |
| 5,320,846 A | 6/1994 | Bistrian et al. |
| 5,326,706 A | 7/1994 | Yland et al. |
| 5,356,771 A | 10/1994 | O'Dell |
| 5,362,622 A | 11/1994 | O'Dell et al. |
| 5,385,821 A | 1/1995 | O'Dell et al. |
| 5,395,314 A | 3/1995 | Klatz et al. |
| 5,434,045 A | 7/1995 | Jost |
| 5,584,804 A | 12/1996 | Klatz et al. |
| 5,586,438 A | 12/1996 | Fahy |
| 5,599,659 A | 2/1997 | Brasile et al. |
| 5,601,972 A | 2/1997 | Meryman |
| 5,629,145 A | 5/1997 | Meryman |
| 5,643,712 A | 7/1997 | Brasile |
| 5,656,154 A | 8/1997 | Meryman |
| 5,696,152 A | 12/1997 | Southard |
| 5,699,793 A * | 12/1997 | Brasile .......................... 600/300 |
| 5,702,881 A | 12/1997 | Brasile et al. |
| 5,707,971 A | 1/1998 | Fahy |
| 5,709,654 A | 1/1998 | Klatz et al. |
| 5,712,084 A * | 1/1998 | Osgood .......................... 435/1.2 |
| 5,716,378 A | 2/1998 | Minten |
| 5,752,929 A | 5/1998 | Klatz et al. |
| 5,827,222 A | 10/1998 | Klatz et al. |
| 5,843,024 A | 12/1998 | Brasile |
| 5,916,800 A | 6/1999 | Elizondo et al. |
| 5,922,598 A | 7/1999 | Mintchev |
| 5,963,335 A | 10/1999 | Boutelle |
| 5,965,433 A | 10/1999 | Gardetto et al. |
| 6,014,864 A | 1/2000 | Owen |
| 6,020,575 A | 2/2000 | Nagle et al. |
| 6,024,698 A | 2/2000 | Brasile |
| 6,046,046 A | 4/2000 | Hassanein |
| 6,060,232 A | 5/2000 | Von Baeyer et al. |
| 6,100,082 A | 8/2000 | Hassanein |

(Continued)

FOREIGN PATENT DOCUMENTS

| | | |
|---|---|---|
| CA | 2722615 A1 | 10/2009 |
| CN | 101322861 A | 12/2008 |

(Continued)

OTHER PUBLICATIONS

Bunegin, et al., Interstitial pO2 and High Energy Phosphates in the Canine Heart during Hypothermic Preservation in a New, Portable, Pulsatile Perfusion Device, from the Department of Anesthesiology University of Texas Health Science Center at San Antonio, Texas; and Center for Cardiovascular Surgery of the Republic of Lithuania, Vilnius, Lithuania, vol. 3, No. 3, Oct. 1998, pp. 1-6.

(Continued)

*Primary Examiner* — Ralph Gitomer
(74) *Attorney, Agent, or Firm* — Thomas C. Meyers; Brown Rudnick LLP

(57) ABSTRACT

Methods of determining the health of an organ, such as a transplant organ, by measuring the ex-situ oxygen consumption rate of the organ. Systems for preserving and transporting organs while monitoring viability by measuring oxygen consumption rates.

13 Claims, 14 Drawing Sheets

(56) References Cited

U.S. PATENT DOCUMENTS

| | | |
|---|---|---|
| 6,174,719 B1 | 1/2001 | Elizondo et al. |
| 6,194,137 B1 | 2/2001 | Khirabadi et al. |
| 6,209,343 B1 | 4/2001 | Owen |
| 6,241,945 B1 | 6/2001 | Owen |
| 6,280,925 B1 | 8/2001 | Brockbank |
| 6,303,388 B1 | 10/2001 | Fahy |
| D453,828 S | 2/2002 | Brassil et al. |
| 6,375,613 B1 | 4/2002 | Brasile |
| 6,406,839 B1 | 6/2002 | Segall et al. |
| 6,475,716 B1 | 11/2002 | Seki |
| 6,485,450 B1 | 11/2002 | Owen |
| 6,492,103 B1 | 12/2002 | Taylor |
| D468,436 S | 1/2003 | Brassil et al. |
| D470,594 S | 2/2003 | Brassil et al. |
| 6,569,615 B1 | 5/2003 | Thatte et al. |
| 6,582,953 B2 | 6/2003 | Brasile |
| 6,596,531 B2 | 7/2003 | Campbell et al. |
| 6,642,019 B1 | 11/2003 | Anderson et al. |
| 6,642,045 B1 | 11/2003 | Brasile |
| 6,656,380 B2 | 12/2003 | Wood et al. |
| 6,673,008 B1 | 1/2004 | Thompson et al. |
| 6,673,594 B1 | 1/2004 | Owen et al. |
| 6,677,150 B2 | 1/2004 | Alford et al. |
| 6,699,231 B1 | 3/2004 | Sterman et al. |
| 6,740,484 B1 | 5/2004 | Khirabadi et al. |
| 6,773,877 B2 | 8/2004 | Fahy |
| 6,794,124 B2 | 9/2004 | Steen |
| 6,794,182 B2 | 9/2004 | Wolf, Jr. |
| 6,905,871 B1 | 6/2005 | Doorschodt et al. |
| 6,924,267 B2 | 8/2005 | Daemen et al. |
| 6,953,655 B1 | 10/2005 | Hassanein et al. |
| 6,977,140 B1 | 12/2005 | Owen et al. |
| 6,994,954 B2 | 2/2006 | Taylor |
| 7,005,253 B2 | 2/2006 | Polyak et al. |
| 7,008,535 B1 | 3/2006 | Spears et al. |
| 7,029,839 B2 | 4/2006 | Toledo-Pereyra et al. |
| D531,319 S | 10/2006 | Schein et al. |
| D531,320 S | 10/2006 | Garland et al. |
| 7,157,222 B2 | 1/2007 | Khirabadi et al. |
| 7,176,015 B2 | 2/2007 | Alford et al. |
| 7,270,946 B2 | 9/2007 | Brockbank et al. |
| 7,294,278 B2 | 11/2007 | Spears et al. |
| 7,316,922 B2 | 1/2008 | Streeter |
| 7,326,564 B2 | 2/2008 | Lundell et al. |
| 7,361,365 B2 | 4/2008 | Birkett et al. |
| 7,410,474 B1 | 8/2008 | Friend et al. |
| 7,504,201 B2 | 3/2009 | Taylor et al. |
| 7,572,622 B2 | 8/2009 | Hassanein et al. |
| 7,651,835 B2 | 1/2010 | Hassanein et al. |
| 7,678,563 B2 | 3/2010 | Wright et al. |
| 7,691,622 B2 | 4/2010 | Garland et al. |
| 7,749,693 B2 | 7/2010 | Brassil et al. |
| 7,811,808 B2 | 10/2010 | van der Plaats et al. |
| 7,824,848 B2 | 11/2010 | Owen et al. |
| 7,897,327 B2 | 3/2011 | Millis et al. |
| 8,097,449 B2 | 1/2012 | Garland et al. |
| 8,268,547 B2 | 9/2012 | Owen et al. |
| 8,268,612 B2 | 9/2012 | Owen et al. |
| 8,304,181 B2 | 11/2012 | Hassanein et al. |
| 8,420,380 B2 | 4/2013 | Fishman et al. |
| 8,465,970 B2 | 6/2013 | Hassanein et al. |
| 8,785,116 B2 * | 7/2014 | Anderson et al. .............. 435/1.2 |
| 8,828,710 B2 | 9/2014 | Anderson et al. |
| 8,835,158 B2 | 9/2014 | Judson et al. |
| 2002/0042131 A1 | 4/2002 | Brockbank et al. |
| 2002/0051779 A1 | 5/2002 | Gage et al. |
| 2002/0064768 A1 | 5/2002 | Polyak et al. |
| 2002/0068360 A1 | 6/2002 | Brockbank et al. |
| 2002/0115634 A1 | 8/2002 | Polyak et al. |
| 2002/0177117 A1 | 11/2002 | Wolf |
| 2003/0022148 A1 | 1/2003 | Seki |
| 2003/0053998 A1 | 3/2003 | Daemen et al. |
| 2003/0118980 A1 | 6/2003 | Taylor |
| 2003/0125804 A1 | 7/2003 | Kruse et al. |
| 2003/0180704 A1 | 9/2003 | Brockbank et al. |
| 2004/0014199 A1 | 1/2004 | Streeter |
| 2004/0038192 A1 | 2/2004 | Brasile |
| 2004/0038193 A1 | 2/2004 | Brasile |
| 2004/0058432 A1 | 3/2004 | Owen et al. |
| 2004/0067480 A1 | 4/2004 | Brockbank et al. |
| 2004/0111104 A1 | 6/2004 | Schein et al. |
| 2004/0170950 A1 | 9/2004 | Prien |
| 2004/0171138 A1 | 9/2004 | Hassanein et al. |
| 2004/0221719 A1 | 11/2004 | Wright et al. |
| 2004/0224298 A1 | 11/2004 | Brassil et al. |
| 2004/0224299 A1 | 11/2004 | Garland et al. |
| 2004/0241634 A1 | 12/2004 | Millis et al. |
| 2004/0248281 A1 | 12/2004 | Wright et al. |
| 2005/0100876 A1 | 5/2005 | Khirabadi et al. |
| 2005/0147958 A1 | 7/2005 | Hassanein et al. |
| 2005/0153271 A1 | 7/2005 | Wenrich |
| 2005/0221269 A1 | 10/2005 | Taylor et al. |
| 2005/0233299 A1 | 10/2005 | Sawa et al. |
| 2005/0255442 A1 | 11/2005 | Brassil et al. |
| 2005/0277106 A1 | 12/2005 | Daemen et al. |
| 2006/0019388 A1 | 1/2006 | Hutmacher et al. |
| 2006/0063142 A1 | 3/2006 | Owen et al. |
| 2006/0121439 A1 | 6/2006 | Baker |
| 2006/0121512 A1 | 6/2006 | Parenteau |
| 2006/0121605 A1 | 6/2006 | Parenteau |
| 2006/0141077 A1 | 6/2006 | Pettersson |
| 2006/0148062 A1 | 7/2006 | Hassanein et al. |
| 2006/0154357 A1 | 7/2006 | Hassanein et al. |
| 2006/0154358 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0009881 A1 | 1/2007 | Arzt et al. |
| 2007/0015131 A1 | 1/2007 | Arzt et al. |
| 2007/0166292 A1 | 7/2007 | Brasile |
| 2007/0184545 A1 | 8/2007 | Plaats et al. |
| 2007/0190636 A1 | 8/2007 | Hassanein et al. |
| 2007/0243518 A1 | 10/2007 | Serna et al. |
| 2007/0275364 A1 | 11/2007 | Hassanein et al. |
| 2008/0017194 A1 | 1/2008 | Hassanein et al. |
| 2008/0070229 A1 | 3/2008 | Streeter |
| 2008/0070302 A1 | 3/2008 | Brockbank et al. |
| 2008/0096184 A1 | 4/2008 | Brasile |
| 2008/0145919 A1 | 6/2008 | Franklin et al. |
| 2008/0187901 A1 | 8/2008 | Doorschodt et al. |
| 2008/0234768 A1 | 9/2008 | Hassanein et al. |
| 2008/0286747 A1 | 11/2008 | Curtis et al. |
| 2008/0288399 A1 | 11/2008 | Curtis et al. |
| 2008/0311552 A1 | 12/2008 | Min |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0226878 A1 | 9/2009 | Taylor et al. |
| 2009/0291486 A1 | 11/2009 | Wenrich |
| 2010/0015592 A1 | 1/2010 | Doorschodt |
| 2010/0028850 A1 | 2/2010 | Brassil |
| 2010/0086907 A1 | 4/2010 | Bunegin et al. |
| 2010/0112542 A1 | 5/2010 | Wright et al. |
| 2010/0151559 A1 | 6/2010 | Garland et al. |
| 2010/0209902 A1 | 8/2010 | Zal et al. |
| 2010/0216110 A1 | 8/2010 | Brockbank |
| 2010/0221696 A1 | 9/2010 | Owen et al. |
| 2010/0233670 A1 | 9/2010 | Gavish |
| 2010/0234928 A1 | 9/2010 | Rakhorst et al. |
| 2011/0033916 A1 | 2/2011 | Hutzenlaub et al. |
| 2011/0039253 A1 | 2/2011 | Owen et al. |
| 2011/0053256 A1 | 3/2011 | Owen et al. |
| 2011/0059429 A1 | 3/2011 | Owen et al. |
| 2011/0129810 A1 | 6/2011 | Owen et al. |
| 2011/0129908 A1 | 6/2011 | Owen et al. |
| 2011/0136096 A1 | 6/2011 | Hassanein et al. |
| 2011/0183310 A1 | 7/2011 | Kravitz et al. |
| 2011/0212431 A1 | 9/2011 | Bunegin et al. |
| 2011/0217689 A1 * | 9/2011 | Bunegin et al. ................ 435/1.2 |
| 2012/0148542 A1 | 6/2012 | Kravitz |
| 2014/0087357 A1 * | 3/2014 | Kohl et al. ..................... 435/1.2 |
| 2014/0314881 A1 * | 10/2014 | Reynolds et al. ............. 424/718 |

(56) References Cited

U.S. PATENT DOCUMENTS

| | | | |
|---|---|---|---|
| 2014/0349273 A1 | 11/2014 | Anderson et al. | |
| 2014/0356850 A1 | 12/2014 | Anderson et al. | |
| 2014/0356933 A1 | 12/2014 | Anderson et al. | |
| 2015/0017627 A1* | 1/2015 | Anderson et al. | 435/1.2 |

FOREIGN PATENT DOCUMENTS

| | | |
|---|---|---|
| DE | 19922310 A1 | 11/2000 |
| DE | 102005048625 A1 | 4/2007 |
| JP | 8-169801 A | 7/1996 |
| JP | 2008-120713 A | 5/2008 |
| WO | 97/43899 A1 | 11/1997 |
| WO | 00/18226 A1 | 4/2000 |
| WO | 00/18226 A2 | 4/2000 |
| WO | 00/60935 A1 | 10/2000 |
| WO | 01/37719 A2 | 5/2001 |
| WO | 01/54495 A1 | 8/2001 |
| WO | 01/78504 A2 | 10/2001 |
| WO | 01/78505 A1 | 10/2001 |
| WO | 01/95717 A2 | 12/2001 |
| WO | 02/17714 A2 | 3/2002 |
| WO | 02/26034 A2 | 4/2002 |
| WO | 02/32225 A2 | 4/2002 |
| WO | 02/89571 A1 | 11/2002 |
| WO | 2004/017838 A2 | 3/2004 |
| WO | 2004/026031 A2 | 4/2004 |
| WO | 2004/052101 A1 | 6/2004 |
| WO | 2004/089085 A2 | 10/2004 |
| WO | 2004/089090 A1 | 10/2004 |
| WO | 2004/105484 A1 | 12/2004 |
| WO | 2004/110146 A1 | 12/2004 |
| WO | 2005/022994 A1 | 3/2005 |
| WO | 2005/074681 A2 | 8/2005 |
| WO | 2005/099588 A2 | 10/2005 |
| WO | 2006/033674 A1 | 3/2006 |
| WO | 2006/042138 A2 | 4/2006 |
| WO | 2006/052133 A2 | 5/2006 |
| WO | 2006/060709 A2 | 6/2006 |
| WO | 2007/111495 A1 | 10/2007 |
| WO | 2007/124044 A2 | 11/2007 |
| WO | 2008/108996 A1 | 9/2008 |
| WO | 2008/144021 A2 | 11/2008 |
| WO | 2008/150587 A2 | 12/2008 |
| WO | 2009/020412 A1 | 2/2009 |
| WO | 2009/041806 A1 | 4/2009 |
| WO | 2009/099939 A2 | 8/2009 |
| WO | 2009/132018 A1 | 10/2009 |
| WO | 2010/096821 A2 | 8/2010 |
| WO | 2011/038251 A1 | 3/2011 |
| WO | WO 2012/125782 * | 9/2012 |

OTHER PUBLICATIONS

Bunegin, et al., The Application of Fluidics Based Technology for Perfusion Preservation of Adult, Human Sized, Canine Hearts, from the Department of Anesthesiology, Health Science Center at San Antonio, University of Texas, vol. 8, No. 1/2 (2003), pp. 73-78.

Bunegin, et al., The Application of Fluidics Technology for Organ Preservation, Biomedical Instrumentation & Technology, Mar./Apr. 2004, pp. 155-164.

Calhoon, et al., Twelve-Hour Canine Heart Preservation With a Simple, Portable Hypothermic Organ Perfusion Device, Ann Thorac Surg 1996:62:91-3.

International Preliminary Report on Patentability for PCT Application No. PCT/US2009/041274.

International Search Report and Written Opinion mailed on Dec. 16, 2013, for International Patent Application No. PCT/US2013/054353, filed Aug. 9, 2013 (8 pages).

International Search Report and Written Opinion mailed on Dec. 9, 2013, for International Patent Application No. PCT/US2013/054365, filed Aug. 9, 2013 (10 pages).

International Search Report for PCT Application No. PCT/US2009/041274.

LifePort Brochure, Organ Recovery Systems, www.organ-recovery.com.

Search Report and Written Opinion for PCT Application No. PCT/US2010/050230.

Steinbrook, The New England Journal of Medicine, Organ Donation after Cardiac Death, Jul. 19, 2007.

Tolstykh, et al., Novel portable hypothermic pulsatile perfusion preservation technology: Improved viability and function of rodent and canine kidneys, Ann Transplant, 2010; 15(3):1-9.

Tolstykh, et al., Perfusion Preservation of Rodent Kidneys in a Portable Preservation Device Based on Fluidics Technology, vol. 73, 1508-1526, No. 9, May 15, 2002.

Wandall, et al., Galactosylation does not prevent the rapid clearance of long-term 40C-stored platelets, Blood, 2008; 111(6):3249-3256.

Weegman, et al., Continuous Real-time Viability Assessment of Kidneys Based on Oxygen Consumption, Transplant Proc. 2010; 42(6): 2020-2023.

* cited by examiner

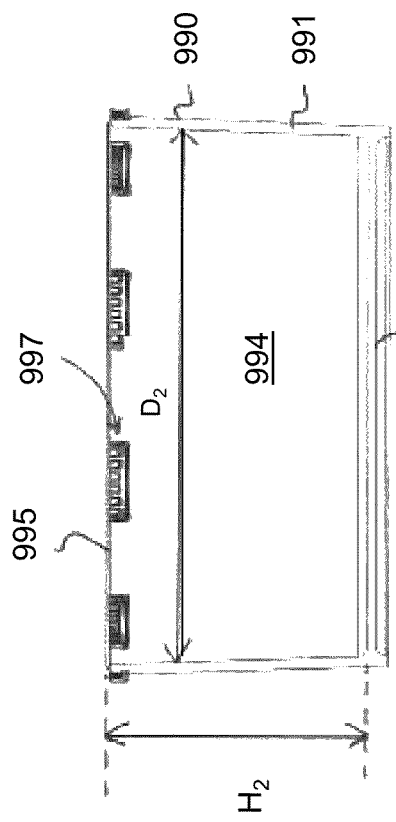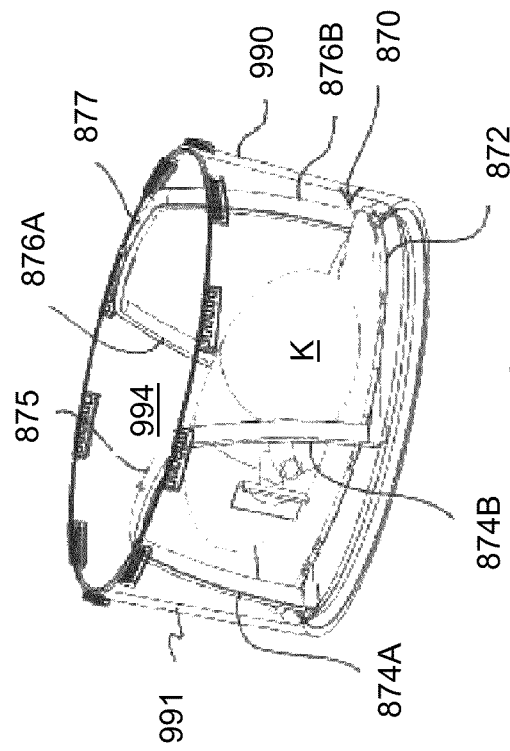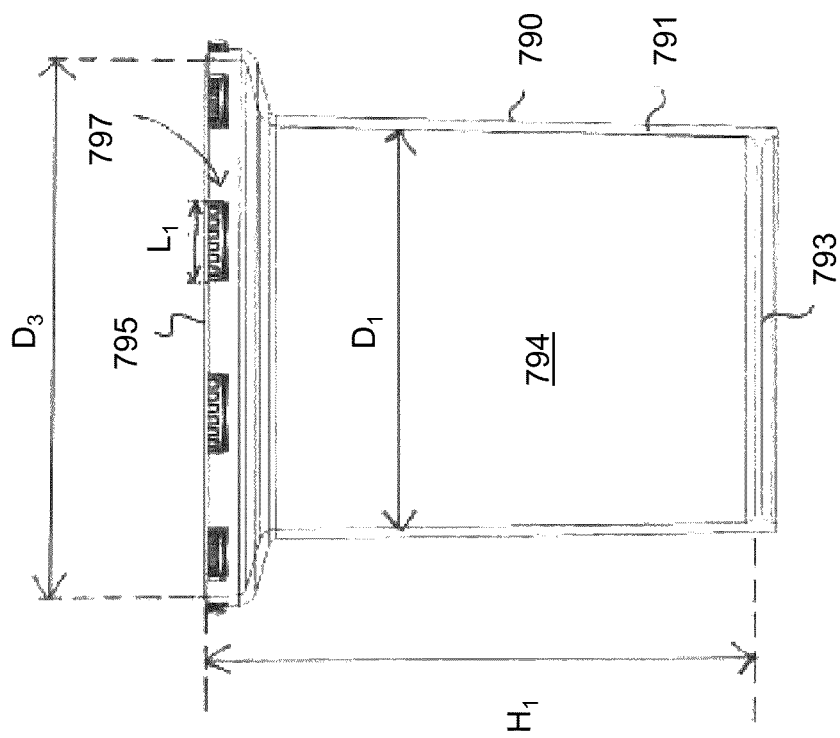

METHODS AND SYSTEMS FOR ASSESSING THE SUITABILITY OF AN ORGAN FOR TRANSPLANT

RELATED APPLICATIONS

This application is a continuation of U.S. patent application Ser. No. 13/572,332, filed Aug. 10, 2012, which is now U.S. Pat. No. 8,785,116, which is incorporated by reference herein in its entirety.

FIELD OF THE INVENTION

The invention relates, generally, to methods for assessing the viability of an organ intended for transplant after the organ has been removed from the donor.

BACKGROUND

Approximately 115,000 Americans are currently awaiting organ donations. Their conditions range from heart disease, to cancer, to birth defects, to combat injury. While approximately 80 Americans per day receive organ transplants, another 18 per day die waiting for a healthy matching organ. (U.S. Department of Health and Human Services, Organ Procurement and Transplantation Network; http://optn.transplant.hrsa.gov/)

While there is a need for more donors, there is also a need for better methods of preserving donated organs and assessing viability between harvest and transplant. In some cases, organs expire for purely logistic reasons, that is, they cannot be delivered to the intended recipient within the mandated time frame. For example, hearts that are preserved by cold static storage (e.g., ice chest) cannot be transplanted after four hours of ischemia (lack of blood supply) for fear that the heart will not function in the recipient. Accordingly, weather and traffic delays can cause an otherwise "perfect match" organ to go unused. The short-comings of cold static organs storage have been addressed by a number of recent innovations, such as those disclosed in U.S. patent application Ser. No. 13/420,962, "Apparatus for Oxygenation and Perfusion of Tissue for Organ Preservation," filed Mar. 15, 2012, and incorporated herein by reference in its entirety.

The "time window" for organ transplant is somewhat arbitrary, however, because the overall health of the donor organ may vary substantially at the time of harvest. For example, the heart of a 50 year old man who died of Alzheimer's will likely not fare as well in ischemic conditions as the heart of an 18-year-old athlete who died in a traffic accident. Certainly, if it were possible to assess the viability of organs during and/or after transport, more organs would be transplanted that were outside the standard transport window.

In addition to monitoring the viability of "healthy" donor organs, reliable assessment techniques could also increase the total number of available donor organs. As discussed above, the demand for donor organs far exceeds the supply. This discrepancy has prompted doctors to re-assess what constitutes a harvestable organ. For many years, organs were only considered for transplant if cardiac death had not preceded harvest or if harvest took place immediately after cardiac death, so-called "beating-heart" donors. Accordingly, donor organs were typically only harvested from patients who died in a hospital capable of providing life support at the time of death.

New research into expanded criteria donors (ECD) and donation after cardiac death (DCD) suggest that many organs that are discarded may be viable for transplant. For example, kidneys are now harvested and transplanted from donors who are over age 60, or over age 50 with a history of hypertension. Additionally, kidneys may be harvested from donors who arrive at the hospital with continued resuscitation after cardiac arrest, but no indication of survival. Kidney donations, in particular, have pushed the limit for donor harvest because a recipient undergoing an unsuccessful transplant can be kept on dialysis indefinitely until a new match is identified.

Nonetheless, doctors have successfully harvested livers from the ECD and DCD groups, and many advocate that this pool of donors is further expanded to include lungs, pancreases, and even hearts. See Steinbrook, "Organ Donation After Cardiac Death," *New England Journal of Medicine,* 357; 3, 210-13 (2007). Systems capable of increasing the transport time of organs while also monitoring the viability of the organs could substantially increase the pool of available organs.

SUMMARY

The invention provides methods for evaluating the viability of an organ that may be used for transplant. In particular, by measuring the oxygen consumption rate of the organ, as the organ is perfused with an oxygen-containing fluid, it is possible to determine the overall health of the organ and its viability for transplant. With the methods of the invention it will be possible to evaluate a transplant organ (e.g. heart, kidney, lung, liver, pancreas) at all stages; from harvest to transplant. This will allow medical professionals to validate, and then use organs which would otherwise be discarded because the organ was outside of the donor body for too long, or because the organ was from an expanded criterion donor. In addition, the invention will save resources in the event that the organ expires prematurely. For example, if a donor organ expires during transport, transport personnel can contact the hospital and tell the transport team to stand down and to not subject the transplant recipient to unnecessary treatments, e.g., anesthesia.

In addition to the methods of evaluating an organ, the invention provides systems for the simultaneous perfusion of donor organs with oxygenated preservation solution and monitoring of the overall oxygen consumption of the organ. This system will allow an organ to be kept viable longer, and allows users (e.g., transport teams) to monitor the health of the organ during transport. Additionally, some systems are capable of monitoring oxygen consumption during preservation and then using the consumption data to alter the perfusion temperature, flow rate, pressure, etc. of the preservation system, thereby optimizing the preservation conditions for the organ. In some embodiments, the system provides a time-varying pressure to the preservation solution, thereby mimicking the pressure differentials that would be found in the vasculature.

The invention also provides methods for predicting a glomerular filtration rate of a kidney by perfusing the kidney with an oxygenated solution and monitoring the oxygen consumption rate of the kidney. The oxygen consumption rate can then be compared to a standard such as a functional kidney consumption rate in order to predict a glomerular filtration rate. For example, a measured oxygen consumption rate of 2.5 $\mu l O_2$/min/g of organ mass or greater may predict a glomerular filtration rate of 0.05 ml fluid/min/g of organ mass or greater. An extension of this method is to use the predicted glomerular filtration rate to determine whether a donor kidney is suitable for transplant, for example when the donor kidney is from an expanded criteria donor (ECD) or from a donation after cardiac death (DCD).

The methods and systems described herein are generally applicable to organs, such as hearts, lungs, livers, pancreases, and kidneys. In particular, the methods will be useful for evaluating and monitoring hearts and kidneys. Nonetheless, the concepts of the invention are broadly applicable to any system containing cells that survive by respiration. Thus, it is possible to monitor the health of tissues or other body parts by monitoring oxygen consumption.

BRIEF DESCRIPTION OF THE DRAWINGS

FIG. 12 is a front view of a perfusion device for use with an embodiment of the invention.

FIG. 13 is a front view of an organ support for use in a perfusion device according to the invention.

FIG. 14 is a perspective view of an organ support for use in a perfusion device according to the invention.

DETAILED DESCRIPTION

Figure 1:
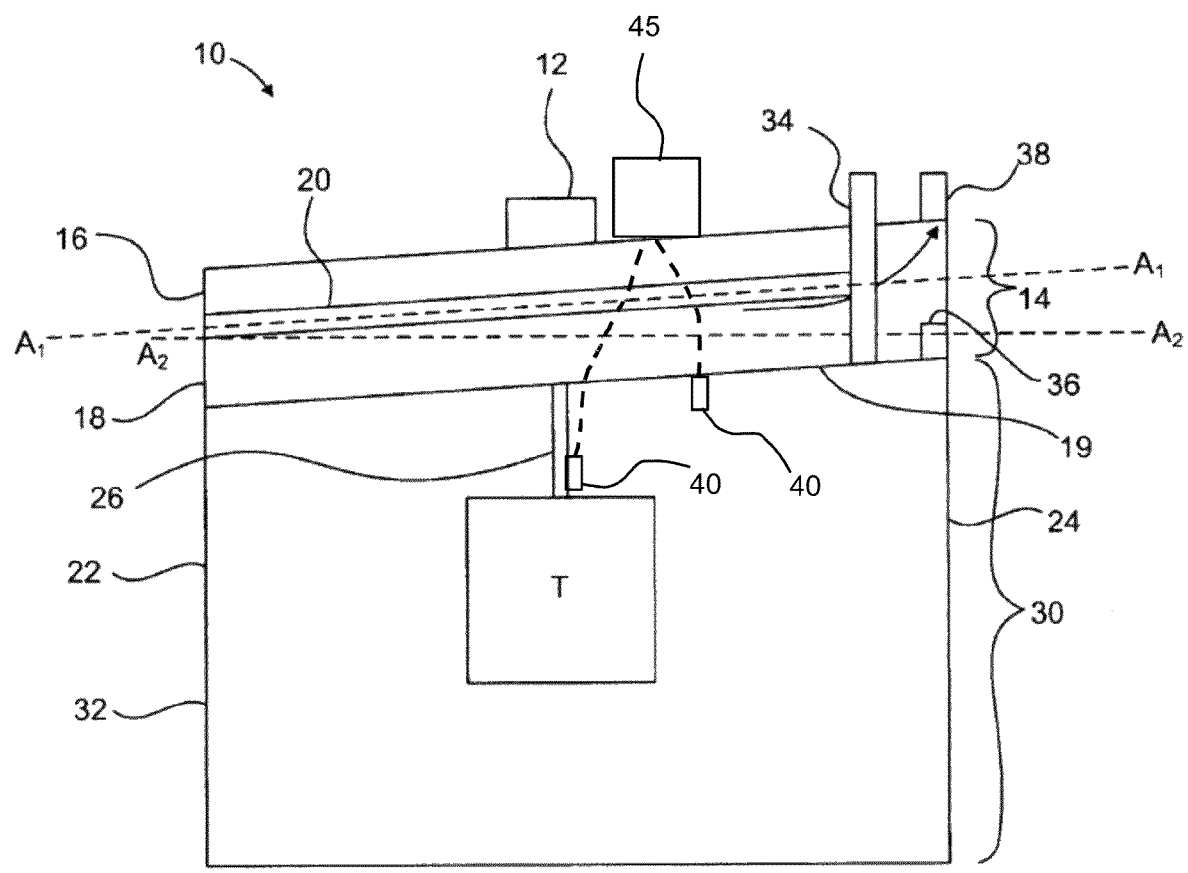
FIG. 1 is a simplified diagram of an embodiment of the invention.

Methods and systems are described herein that are configured to monitor the health of an organ or determine the suitability of an organ for transplant. In preferred embodiments, the oxygen consumption rate of the organ is measured and correlated with the health of the organ or the suitability of the organ for transplant. Additionally, systems of the invention may oxygenate and perfuse an organ with variable pressure while measuring the oxygen consumption rate of the organ. The perfusion devices described may be portable devices, thereby extending the viability of the organ over a longer period of time. Portable extracorporeal preservation is desirable for transporting organs to be transplanted from a donor to a recipient.

The oxygen consumption rate of an organ (or a tissue or other organism) is the amount of oxygen consumed per unit of time, presumably due to cellular respiration of the organ. A measurement of the oxygen consumption rate gives clues to the health of the organ/tissue exposed to the oxygen. Organs or tissues consuming oxygen in a range of "normal" (i.e., functional) rates are presumed healthy, while organs or tissues consuming oxygen at less than the "normal" (i.e., functional) rate are likely unhealthy, e.g., experiencing cellular death. Various previous studies or new studies may be used to determine a functional oxygen consumption rate for comparison to the measured oxygen consumption rate. The functional oxygen consumption rate for an organ may be, for example, 10 nmol$O_2$/min/g of organ mass or greater, 20 nmol$O_2$/min/g of organ mass or greater, 50 nmol$O_2$/min/g of organ mass or greater, 80 nmol$O_2$/min/g of organ mass or greater, or 100 nmol$O_2$/min/g of organ mass or greater. The oxygen consumption rate may be dependent upon the temperature of the organ or tissue, and the overall rate may be indexed as a function of mass to account for a larger number of cells.

In an embodiment of the invention, the oxygen consumption rate is calculated as a function of the partial pressure of oxygen in a fluid which is flowing through the organ (e.g., a perfusate). Thus, by measuring a partial pressure into and out of the organ, an oxygen consumption rate can be calculated. Alternatively, the oxygen consumption rate may be calculated by measuring the partial pressure of oxygen in a fluid before and after the fluid contacts an organ or tissue. The fluid may be a gas, for example air, or the fluid may be a liquid, for example blood or a preservation fluid. In the case of a fluid moving through an organ, the oxygen consumption rate (OCR) can be calculated from $$OCR = \frac{Q \times (pO_{2,in} - pO_{2,out}) \times a}{m}$$

wherein Q is the flow of the fluid through the organ, $pO_{2,in}$ is the partial pressure of oxygen in the fluid entering the organ, $pO_{2,out}$ is the partial pressure of oxygen in the fluid exiting the organ, a is the solubility of oxygen in the fluid at a given temperature (typically given in mol/ml·mmHg), and m is the organ mass.

For a given type of organ or tissue, an oxygen consumption rate in the "normal" range is indicative of a healthy organ. The OCR value will vary between organs, in response to the type of tissue comprising the organ, however the OCR value will typically be greater than 50 nmol$O_2$/min/g of organ mass, e.g. greater than 100 nmol$O_2$/min/g of organ mass, e.g. greater than 150 nmol$O_2$/min/g of organ mass, e.g. greater than 200 nmol$O_2$/min/g of organ mass.

Additionally, in the case of organs harvested to be used for transplant, a measurement of the OCR can provide an instantaneous status of the organ health. For example, an OCR measurement immediately prior to transplant can be a "final check" of transplant organ viability. Additionally, OCR measurements can be used to determine if an organ, that has exceeded the transport window, is still viable for transplant. Alternatively, an organ, e.g. a kidney, harvested from an extended candidate or from a cardiac death can be evaluated for suitability as a transplant organ after removal from the donor.

In preferred embodiments, OCR measurement on a transplant organ will be continuous throughout the transport of the organ, thereby allowing medical professionals to know the health of the organ at all times and/or intervene in the event that the organ does not maintain an OCR within a "normal" range. In some embodiments, a transplant container, for example a hypothermic perfusion device, will have oxygen sensors and a processor which communicates the OCR measurement to the control systems of the perfusion device. Thus, the perfusion device can modify the level of oxygenation or rate of perfusion in response to changes in OCR levels for the organ, thereby keeping the organ healthy during transport. The OCR measurement may also be communicated to a communication device, for example a digital readout or an audible signal or a warning light to alert a user that the OCR has fallen out of the "normal" range.

A number of perfusion devices, e.g., hypothermal perfusion devices, can be used with the methods of the invention. For example, the devices disclosed in U.S. patent application Ser. No. 13/420,962, "Apparatus for Oxygenation and Perfusion of Tissue for Organ Preservation," filed Mar. 15, 2012, and incorporated herein by reference in its entirety. Typically, the perfusion devices will incorporate at least one oxygen sensor, e.g., two oxygen sensors, to measure a partial pressure of oxygen into and out of the organ. In some embodiments, the partial pressure of oxygen into the organ will be measured just prior to the oxygenated perfusate entering the organ, and the partial pressure of the perfusate exiting the organ will be measured just after leaving the organ, and the measurements compared to determine a rate of oxygen consumption. In other embodiments, the partial pressure of oxygen in an oxygenation/pump chamber will be measured, and the partial pressure of oxygen in an organ storage chamber (into which the perfusate drains after perfusing the organ) will be measured, and the measurements compared to determine a rate of oxygen consumption. In other embodiments, the partial pressure of the oxygen may be measured at different locations prior to and after the organ is perfused.

In some embodiments, a device for use with the invention is configured to self-purge excess fluid (e.g., liquid and/or gas). For example, in some embodiments, a device includes a lid assembly in which at least a portion of the lid assembly is inclined with respect to a horizontal axis. The inclined portion of the lid assembly is configured to facilitate the flow of fluid towards a purge port disposed at substantially the highest portion of a chamber of the lid assembly. In this manner, excess fluid can escape the device via the purge port. Also in this manner, when excess liquid is expelled from the device via the purge port, an operator of the device can determine that any excess gas has also been purged from the device, or at least from within an organ chamber of the device, because the gas is lighter than the liquid and will move towards and be expelled via the purge port before excess liquid.

In some embodiments, a device is configured to pump oxygen through a pumping chamber to oxygenate a perfusate and to perfuse a bodily tissue based on a desired control scheme. For example, in some embodiments, the device includes a pneumatic system configured to deliver oxygen to the pumping chamber on a time-based control scheme. The pneumatic system can be configured to deliver oxygen to the pumping chamber for a first period of time. The pneumatic system can be configured to vent oxygen and carbon dioxide from the pumping chamber for a second period of time subsequent to the first period of time. In another example, in some embodiments, the device includes a pneumatic system configured to deliver oxygen to the pumping chamber on a pressure-based control scheme. The pneumatic system can be configured to deliver oxygen to the pumping chamber until a first threshold pressure is reached within the pumping chamber. The pneumatic system can be configured to vent oxygen and carbon dioxide from the pumping chamber until a second threshold pressure is reached within the pumping chamber. In some embodiments, a power source of the device is in use when oxygen is being delivered to the pumping chamber and is not in use when oxygen and carbon dioxide are being vented from the pumping chamber. In this manner, the device is configured to help minimize usage of the power source, and thus the device can prolong the period of time an organ is extracorporeally preserved within the device before the power source is depleted. Such an improvement increases the time available for transporting organs from a donor to a recipient. Such an improvement also facilitates the long term preservation of the organ, such as for a period of scientific research.

An apparatus 10 suitable for use with the methods of the invention is shown schematically in FIG. 1. The apparatus 10 is configured to oxygenate a perfusate (not shown) received in a pumping chamber 14 of the apparatus. The apparatus 10 includes a valve 12 configured to permit a fluid (e.g., oxygen) to be introduced into a first portion 16 of the pumping chamber 14. A membrane 20 is disposed between the first portion 16 of the pumping chamber 14 and a second portion 18 of the pumping chamber. The membrane 20 is configured to permit the flow of a gas between the first portion 16 of the pumping chamber 14 and the second portion 18 of the pumping chamber through the membrane. The membrane 20 is configured to substantially prevent the flow of a liquid between the second portion 18 of the pumping chamber 14 and the first portion 16 of the pumping chamber through the membrane. In this manner, the membrane can be characterized as being semi-permeable.

The membrane 20 is disposed within the pumping chamber 14 along an axis A1 that is transverse to a horizontal axis A2. Said another way, the membrane 20 is inclined, for example, from a first side 22 to a second side 24 of the apparatus 10. As such, as described in more detail below, a rising fluid in the second portion 18 of the pumping chamber 14 will be directed by the inclined membrane 20 towards a port 38 disposed at the highest portion of the pumping chamber 14. The port 38 is configured to permit the fluid to flow from the pumping chamber 14 into the atmosphere external to the apparatus 10. In some embodiments, the port 38 is configured for unidirectional flow, and thus is configured to prevent a fluid from being introduced into the pumping chamber 14 via the port (e.g., from a source external to the apparatus 10). In some embodiments, the port 38 includes a luer lock.

The second portion 18 of the pumping chamber 14 is configured to receive a fluid. In some embodiments, for example, the second portion 18 of the pumping chamber 14 is configured to receive a liquid perfusate. The second portion 18 of the pumping chamber 14 is in fluid communication with an adapter 26. The adapter 26 is configured to permit movement of the fluid from the pumping chamber 14 to an organ, for example, a heart. In some embodiments, the pumping chamber 14 defines an aperture (not shown) configured to be in fluidic communication with a lumen (not shown) of the adapter 26. The adapter 26 is configured to be coupled to the transplant organ (T). The adapter 26 can be coupled to the transplant organ (T) in any suitable manner. For example, in some embodiments, the adapter 26 is configured to be sutured to the transplant organ (T). In another example, the adapter 26 is coupleable to the transplant organ (T) via an intervening structure, such as silastic or other tubing. In some embodiments, at least a portion of the adapter 26, or the intervening structure, is configured to be inserted into the transplant organ (T). For example, in some embodiments, the lumen of the adapter 26 (or a lumen of the intervening structure) is configured to be fluidically coupled to a vessel of the transplant organ (T). In some embodiments, the vessel of the transplant organ (T) may be coupled to the adapter 26 with a clamp, suture, or tie.

In some embodiments, the adapter 26 is configured to support the transplant organ (T) when the transplant organ (T) is coupled to the adapter. For example, in some embodiments, the adapter 26 includes a retention mechanism (not shown) configured to be disposed about at least a portion of the transplant organ (T) and to help retain the transplant organ (T) with respect to the adapter. The retention mechanism can be, for example, a net, a cage, a sling, or the like. In some embodiments, the apparatus 10 includes a basket (not shown) or other support mechanism configured to support the transplant organ (T) when the transplant organ (T) is coupled to the adapter 26 or otherwise received in the apparatus 10.

An organ chamber 30 is configured to receive the transplant organ (T) and a fluid. In some embodiments, the apparatus 10 includes a port 34 that is extended through the apparatus 10 (e.g., through the pumping chamber 14) to the organ chamber 30. The port 34 is configured to permit fluid (e.g., perfusate) to be introduced to the organ chamber 30. In this manner, fluid can be introduced into the organ chamber 30 as desired by an operator of the apparatus. For example, in some embodiments, a desired amount of perfusate is introduced into the organ chamber 30 via the port 34, such as before disposing the transplant organ (T) in the organ chamber 30 and/or while the transplant organ (T) is received in the organ chamber. In some embodiments, the port 34 is a unidirectional port, and thus is configured to prevent the flow of fluid from the organ chamber 30 to an area external to the organ chamber through the port. In some embodiments, the port 34 includes a luer lock. The organ chamber 30 may be of any suitable volume necessary for receiving the transplant organ (T) and a requisite amount of fluid for maintaining viability of the transplant organ (T). In one embodiment, for example, the volume of the organ chamber 30 is approximately 2 liters.

The organ chamber 30 is formed by a canister 32 and a bottom portion 19 of the pumping chamber 14. In a similar manner as described above with respect to the membrane 20, an upper portion of the organ chamber (defined by the bottom portion 19 of the pumping chamber 14) can be inclined from the first side 22 towards the second side 24 of the apparatus. In this manner, as described in more detail below, a rising fluid in the organ chamber 30 will be directed by the inclined upper portion of the organ chamber towards a valve 36 disposed at a highest portion of the organ chamber. The valve 36 is configured to permit a fluid to flow from the organ chamber 30 to the pumping chamber 14. The valve 36 is configured to prevent flow of a fluid from the pumping chamber 14 to the organ chamber. The valve 36 can be any suitable valve for permitting unidirectional flow of the fluid, including, for example, a ball check valve.

The canister 32 can be constructed of any suitable material. In some embodiments, the canister 32 is constructed of a material that permits an operator of the apparatus 10 to view at least one of the transplant organ (T) or the perfusate received in the organ chamber 30. For example, in some embodiments, the canister 32 is substantially transparent. In another example, in some embodiments, the canister 32 is substantially translucent. The organ chamber 30 can be of any suitable shape and/or size. For example, in some embodiments, the organ chamber 30 can have a perimeter that is substantially oblong, oval, round, square, rectangular, cylindrical, or another suitable shape.

In use, the transplant organ (T) is coupled to the adapter 26. The pumping chamber 14 is coupled to the canister 32 such that the transplant organ (T) is received in the organ chamber 30. In some embodiments, the pumping chamber 14 and the canister 32 are coupled such that the organ chamber 30 is hermetically sealed. A desired amount of perfusate is introduced into the organ chamber 30 via the port 34. The organ chamber 30 can be filled with the perfusate such that the perfusate volume rises to the highest portion of the organ chamber. The organ chamber 30 can be filled with an additional amount of perfusate such that the perfusate flows from the organ chamber 30 through the valve 36 into the second portion 18 of the pumping chamber 14. The organ chamber 30 can continue to be filled with additional perfusate until all atmospheric gas that initially filled the second portion 18 of the pumping chamber 14 rises along the inclined membrane 20 and escapes through the port 38. Because the gas will be expelled from the pumping chamber 14 via the port 38 before any excess perfusate is expelled (due to gas being lighter, and thus more easily expelled, than liquid), an operator of the apparatus 10 can determine that substantially all excess gas has been expelled from the pumping chamber when excess perfusate is released via the port. As such, the apparatus 10 can be characterized as self-purging. When perfusate begins to flow out of the port 38, the apparatus 10 is in a "purged" state (i.e., all atmospheric gas initially within the organ chamber 30 and the second portion 18 of the pumping chamber 14 has been replaced by perfusate). When the purged state is reached, the operator can close both ports 34 and 38, preparing the apparatus 10 for operation.

Oxygen (or another suitable fluid, e.g., gas) is introduced into the first portion 16 of the pumping chamber 14 via the valve 12. A positive pressure generated by the introduction of oxygen into the pumping chamber 14 causes the oxygen to be diffused through the semi-permeable membrane 20 into the second portion 18 of the pumping chamber. Because oxygen is a gas, the oxygen expands to substantially fill the first portion 16 of the pumping chamber 14. As such, substantially the entire surface area of the membrane 20 between the first portion 16 and the second portion 18 of the pumping chamber 14 is used to diffuse the oxygen. The oxygen is diffused through the membrane 20 into the perfusate received in the second portion 18 of the pumping chamber 14, thereby oxygenating the perfusate.

In the presence of the positive pressure, the oxygenated perfusate is moved from the second portion 18 of the pumping chamber 14 into the transplant organ (T) via the adapter 26. For example, the positive pressure can cause the perfusate to move from the pumping chamber 14 through the lumen of the adapter 26 into the vessel of the transplant organ (T). The positive pressure is also configured to help move the perfusate through the transplant organ (T) such that the transplant organ (T) is perfused with oxygenated perfusate.

After the perfusate is perfused through the transplant organ (T), the perfusate is received in the organ chamber 30. In this manner, the perfusate that has been perfused through the transplant organ (T) is combined with perfusate previously disposed in the organ chamber 30. In some embodiments, the volume of perfusate received from the transplant organ (T) following perfusion combined with the volume of perfusate previously disposed in the organ chamber 30 exceeds a volume (e.g., a maximum fluid capacity) of the organ chamber 30. A portion of the organ chamber 30 is flexible and expands to accept this excess volume. The valve 12 can then allow oxygen to vent from the first portion 16 of the pumping chamber 14, thus, reducing the pressure in the pumping chamber 14. As the pressure in the pumping chamber 14 drops, the flexible portion of the organ chamber 30 relaxes, and the excess perfusate is moved through the valve 36 into the pumping chamber 14. The cycle of oxygenating perfusate and perfusing the transplant organ (T) with the oxygenated perfusate can be repeated as desired.

Throughout the process, the partial pressure of oxygen in the perfusate may be monitored with oxygen sensors 40. Oxygen sensors may be optical (e.g., induced fluorescence, fluorescence quenching in presence of oxygen, light absorbance of oxygen-binding molecule), electrical (e.g., Clark-type electrode, lambda sensor), or electromechanical. The oxygen sensors 40 are linked to a sensor processor 45 which may be part of a larger assembly which includes, optionally, a display (e.g., digital readout, indicator lights) and/or audible alerts (e.g., tones, buzzer, beeper). As shown in FIG. 1, two oxygen sensors 40 may be used. The first oxygen sensor 40 may be in fluidic communication with the adapter 26, and used to measure the partial pressure of oxygen in the perfusate entering the transplant organ (T). The second oxygen sensor 40 may be in fluidic communication with the organ chamber 30, and used to measure the partial pressure of oxygen in the perfusate after it has perfused transplant organ (T). The sensor processor may also be linked to a network, e.g., the internet, through a wireless connection or by accessing a mobile phone network, thereby allowing the device to alert a user if the oxygen consumption rate is unstable or lower than a value.

Figure 2:
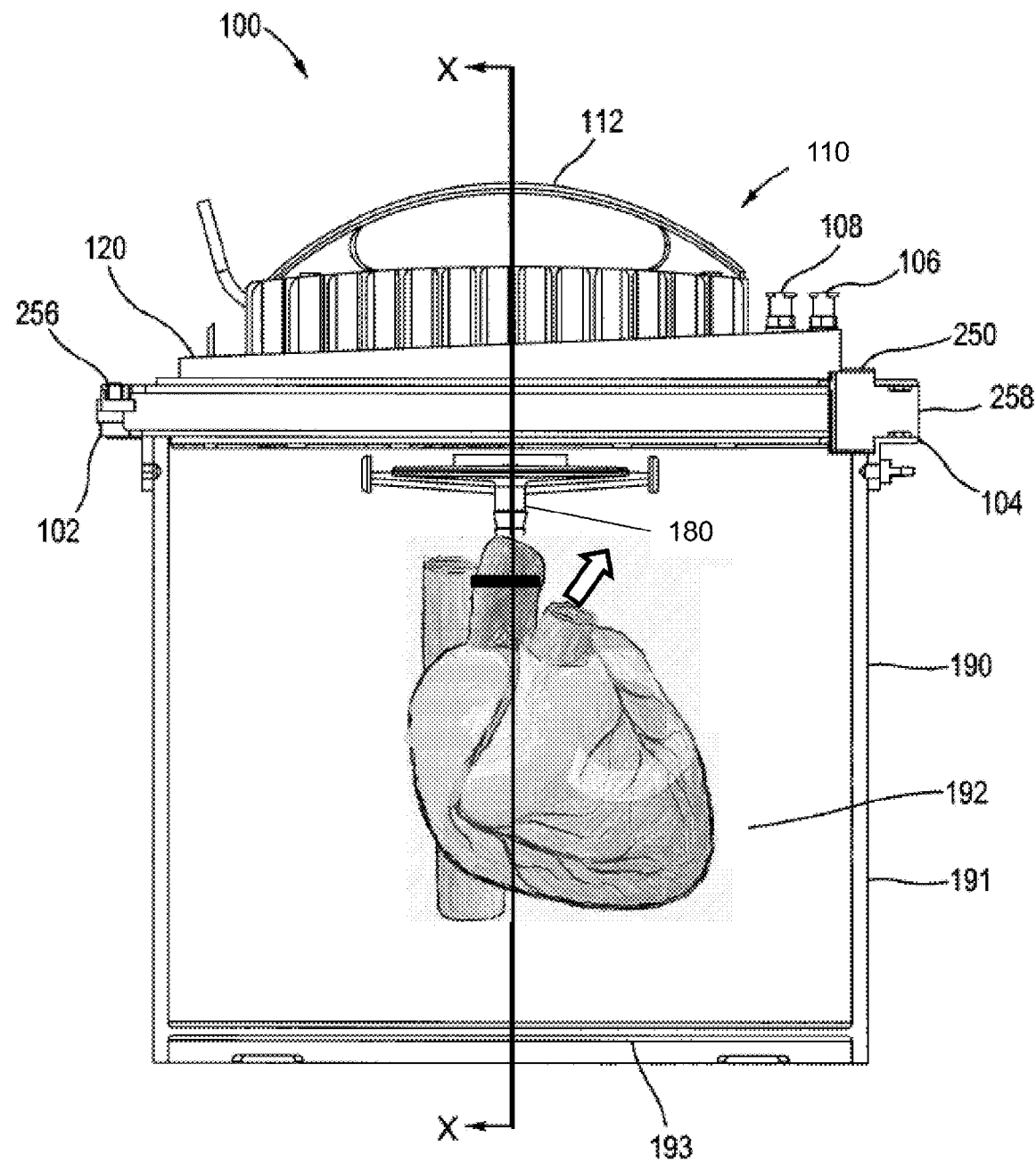
FIG. 2 is a diagram of an embodiment of a perfusion device for use with an embodiment of the invention.
Figure 3:
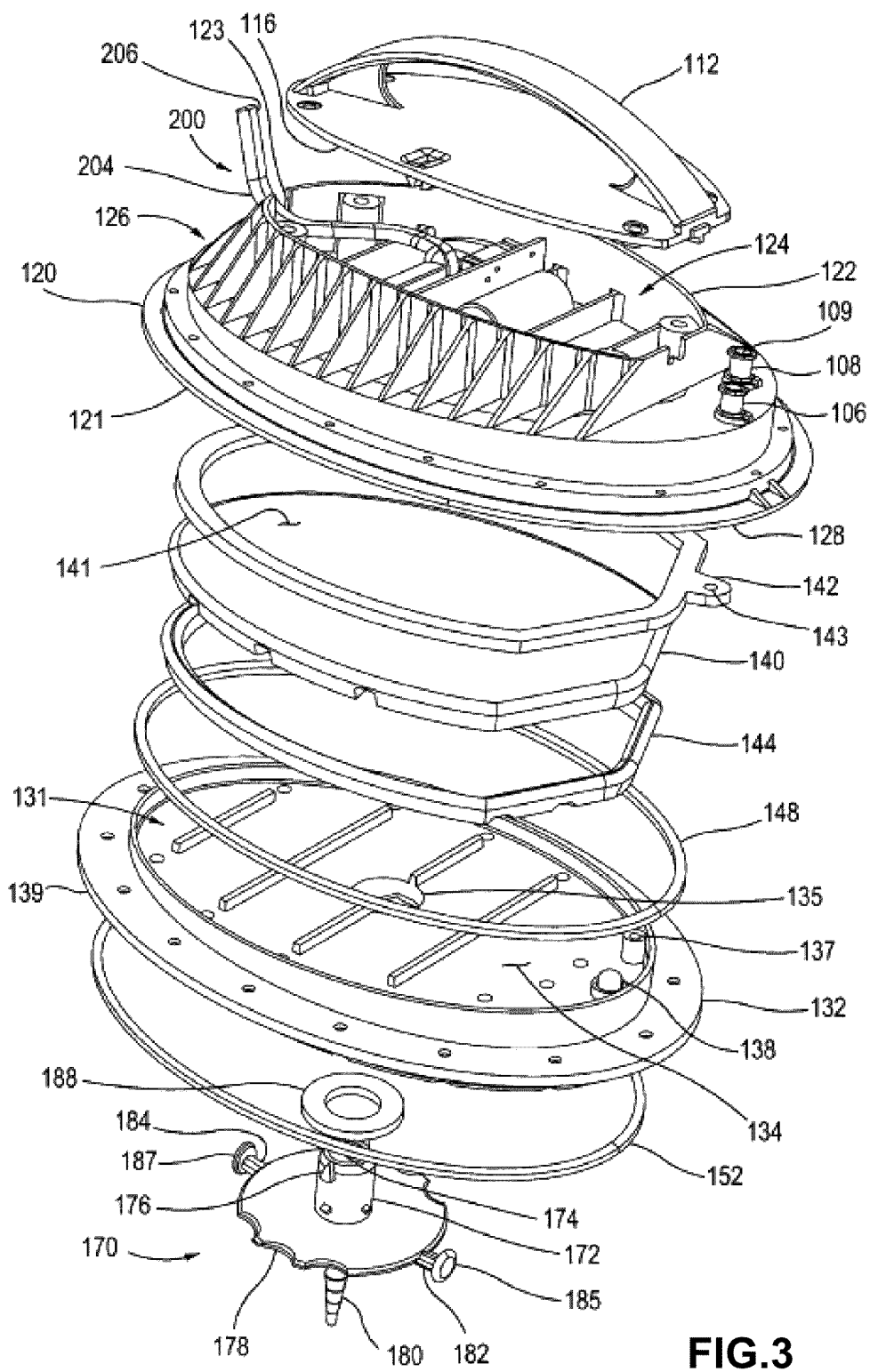
FIG. 3 is an exploded diagram of a perfusion lid for use with an embodiment of the invention.

An alternative apparatus 100 suitable for use with the methods and systems of the invention is illustrated in FIGS. 2-3. The apparatus 100 is configured to oxygenate a perfusate and to perfuse a bodily tissue for extracorporeal preservation of the bodily tissue. The apparatus 100 includes a lid assembly 110, a canister 190, and a coupling mechanism 250.

The apparatus 100 can provide a time-varying pressure on the perfusate which is used to perfuse the transplant organ, for example a heart, however various other organs (kidney, lung, pancreas, liver) could be used. The apparatus may provide a time-varying pressure with a cycle of 0.01 Hz or greater, e.g., 0.05 Hz or greater, e.g., 0.1 Hz or greater, e.g., 0.5 Hz or greater, e.g., 1 Hz or greater. The waveform of the pressure cycle may be sinusoidal, a square wave, saw-tooth, or a combination thereof. The period of the pressure waveform may be constant, or the period may vary. In some instances, the period of the pressure waveform may vary as a function of the temperature of the perfusate.

The lid assembly 110 is configured to facilitate transportability of the apparatus. The lid assembly 110 includes a handle 112 and a lid 120. The handle 112 is configured to be grasped, e.g., by a hand of a person transporting the apparatus 100. The handle 112 is coupled to the lid 120. The handle 112 can be coupled to the lid 120 using any suitable mechanism for coupling. For example, the handle 112 can be coupled to the lid 120 with at least one screw, an adhesive, a hook and loop fastener, mating recesses, or the like, or any combination of the foregoing. An upper portion 122 of the lid 120 defines a chamber 124 configured to receive components of a pneumatic system 200 and a control system 500, each of which is described in more detail below. A bottom portion 116 of the handle 112 is configured to substantially enclose a top of the chamber 124 defined by the lid 120.

The lid assembly 110 defines a pumping chamber configured to receive a gas, such as oxygen, from the pneumatic system 200 (FIG. 4), to facilitate diffusion of the oxygen into a perfusate (not shown) and to facilitate movement of the oxygenated perfusate into an organ, e.g., a transplant organ, e.g., a heart. Although the apparatus 100 is described herein as being configured for use with oxygen, any suitable gas may be used with apparatus 100 instead of or in addition to oxygen. A top of the pumping chamber is formed by a lower portion 128 of the lid 120. A bottom of the pumping chamber is formed by an upper surface 134 of a base 132 of the lid assembly 110.

As illustrated in an exploded perspective view in FIG. 3, the lid assembly 110 includes a first gasket 142, a membrane 140, and a membrane frame 144. The membrane 140 is disposed within the pumping chamber. The first gasket 142 is disposed between the membrane 140 and the lid 120 such that the first gasket is engaged with an upper surface 141 of the membrane 140 and the lower portion 128 of the lid. The first gasket 142 is configured to seal a perimeter of a first portion 127 of the pumping chamber formed between the lower portion 128 of the lid 120 and the upper surface 141 of the membrane 140. In other words, the first gasket 142 is configured to substantially prevent lateral escape of the oxygen from the first portion 127 of the pumping chamber to a different portion of the pumping chamber. In the embodiment illustrated in FIG. 3, the first gasket 142 has a perimeter substantially similar in shape to a perimeter defined by the membrane 140 (e.g., when the membrane is disposed on the membrane frame 148). In other embodiments, however, a first gasket can have another suitable shape for sealing a first portion of a pumping chamber configured to receive oxygen from a pneumatic system.

The first gasket 142 can be constructed of any suitable material. In some embodiments, for example, the first gasket 142 is constructed of silicone, an elastomer, or the like. The first gasket 142 can have any suitable thickness. For example, in some embodiments, the first gasket 142 has a thickness within a range of about 0.1 inches to about 0.15 inches. More specifically, in some embodiments, the first gasket 142 has a thickness of about 0.125 inches. The first gasket 142 can have any suitable level of compression configured to maintain the seal about the first portion 142 of the pumping chamber when the components of the lid assembly 110 are assembled. For example, in some embodiments, the first gasket 142 is configured to be compressed by about 20 percent. In some embodiments, the first gasket 142 can provide a leak-proof seal under operating pressures up to 5 pounds per square inch (psi).

The membrane 140 is configured to permit diffusion of the gas from the first portion 127 of the pumping chamber through the membrane to a second portion 129 of the pumping chamber, and vice versa. The membrane 140 is configured to substantially prevent a liquid (e.g., the perfusate) from passing through the membrane. In this manner, the membrane 140 can be characterized as being semi-permeable. A membrane frame 144 is configured to support the membrane 140 (e.g., during the oxygenation and perfusing of the bodily tissue). The membrane frame 144 can be a substantially ring-like structure with an opening at its center. At least a portion of the membrane 140 is disposed (e.g., wrapped) about at least a portion of the membrane frame 144. In some embodiments, the membrane 140 is stretched when it is disposed on the membrane frame 144. The membrane 140 is disposed about a lower edge of the membrane frame 144 such that the membrane 140 is engaged with a series of protrusions configured to help retain the membrane with respect to the membrane frame 144. At least a portion of the series of protrusions on the lower edge of the membrane frame 144 are configured to be received in a recess 147 defined by the upper surface 134 of the base 132. As such, the membrane 140 is engaged between the membrane frame 144 and the base 132, which facilitates retention of the membrane with respect to the membrane frame. In some embodiments, the first gasket 142 also helps to maintain the membrane 140 with respect to the membrane frame 144 because the first gasket is compressed against the membrane. The membrane 140 is disposed within the pumping chamber at an angle with respect to a horizontal axis. In this manner, the membrane 140 is configured to facilitate the movement of fluid towards a highest portion of the pumping chamber, as described in more detail herein.

The membrane 140 can be of any suitable size. For example, in some embodiments, the upper surface 141 of the membrane 140 can be about 15 to about 20 square inches. More specifically, in some embodiments, the upper surface 141 of the membrane 140 can be about 19 square inches. In another example, the membrane 140 can have any suitable thickness. In some embodiments, for example, the membrane 140 is about 0.005 inches to about 0.010 inches thick. More specifically, in some embodiments, the membrane is about 0.0075 inches thick. The membrane 140 can be constructed of any suitable material. For example, in some embodiments, the membrane is constructed of silicone, plastic, or another suitable material. In some embodiments, the membrane is flexible. As illustrated in FIG. 3, the membrane 140 can be substantially seamless. In this manner, the membrane 140 is configured to be more resistant to being torn or otherwise damaged in the presence of a flexural stress caused by a change pressure in the pumping chamber due to the inflow and/or release of oxygen.

The lid 120 includes a purge port 106 disposed at the highest portion of the second portion 129 of the pumping chamber, as shown in FIG. 2. In some embodiments, the port 106 is disposed at the highest portion of the pumping chamber as a whole. In other words, the highest portion of the second portion 129 of the pumping chamber can be the highest portion of the pumping chamber. The purge port 106 is configured to permit movement of a fluid from the pumping chamber to an area external to the apparatus 100. The purge port 106 can be similar in many respects to a port described herein (e.g., port 38, described above). The purge port 106 can be any suitable mechanism for permitting movement of the fluid from the pumping chamber into the atmosphere external to the apparatus 100, including, but not limited to, a luer lock fitting. The purge port 106 can include a cap (not shown) coupled to the port via a retaining strap.

In some embodiments, the lid 120 is transparent, either in its entirety or in part (e.g. in the vicinity of the purge port 106). This permits a user to readily view a fluid therein (e.g., any gas bubbles) and to confirm completion of purging of excess fluid (e.g., the gas bubbles).

Referring to FIG. 3, and as noted above, the upper surface 134 of the base 132 forms the bottom portion of the pumping chamber. The upper surface 134 of the base 132 is inclined from a first end 102 of the apparatus 100 to a second end 104 of the apparatus. Said another way, the upper surface 134 lies along a plane having an axis different than the horizontal axis. Because each of the first gasket 142, the membrane 140, and the membrane frame 144 are disposed on the upper surface 134 of the base 132, each of the first gasket, the membrane, and the membrane frame are similarly inclined from the first end 102 of the apparatus 100 towards the second end 104 of the apparatus. In this manner, the base 132 is configured to facilitate movement of a fluid towards the highest portion of the pumping chamber. The angle of incline of these components may be of any suitable value to allow fluid (e.g., gas bubbles, excess liquid) to flow towards the purge port 106 and exit the pumping chamber. In some embodiments, the angle of incline is approximately in the range of 1°-10°, in the range of 2°-6°, in the range of 2.5°-5°, in the range of 4°-5° or any angle of incline in the range of 1 (e.g., approximately 1°, $2°$, $3°$, $4°$, $5°$, $6°$, $7°$, $8°$, 9°, 10°).

As illustrated in FIG. 3, a valve 138 is disposed at approximately the highest portion of the lower surface 136 of the base 132. The valve 138 is moveable between an open configuration and a closed configuration. In its open configuration, the valve 138 is configured to permit movement of a fluid from an organ chamber 192, which is defined by the canister 190 and a lower surface 136 of the lid assembly 110, to the pumping chamber via the valve. Specifically, the valve 138 is configured to permit fluid to move from the organ chamber 192 into the second portion 129 of the pumping chamber 114. In this manner, an excess amount of fluid within the organ chamber 192 can overflow through the valve 138 and into the pumping chamber. In its closed configuration, the valve 138 is configured to substantially prevent movement of a fluid from the pumping chamber to the organ chamber 192 via the valve. The valve 138 is moved from its closed configuration to its open configuration when a pressure in the organ chamber 192 is greater than a pressure in the pumping chamber. In some embodiments, the valve 138 is moved from its open position to its closed position when a pressure in the pumping chamber is greater than a pressure in the organ chamber 192 (FIG. 2). The valve 138 can be biased towards its closed configuration. In some embodiments, one or more additional valves (not shown) are disposed at other locations of the base 132. In some embodiments, an additional valve (not shown) is located at approximately the lowest portion of the lower surface 136 of the base 132.

As illustrated in FIGS. 2 and 3, in some embodiments, the valve 138 is a ball check valve. In its closed configuration, a spherical ball of the valve 138 is disposed on a seat of the valve. In its open configuration, the ball is lifted off of the seat of the valve 138. The ball of the valve 138 has a near neutral buoyancy. As such, the ball of the valve 138 will neither sink nor rise merely because it is in the presence of a fluid (e.g., the perfusate, oxygen, or another fluid). The ball of the valve 138 is configured to rise off of the seat of the valve when the pressure in the organ chamber 192 is greater than the pressure in the pumping chamber. In some embodiments, a protrusion 151 of the lid 120 is extended downwardly over the valve 138 to prevent the ball from rising too high above the seat such that the ball could be laterally displaced with respect to the seat. In some embodiments, the ball of the valve 138 is configured to return to the seat of the valve when the pressure in the pumping chamber is greater than the pressure in the organ chamber. In some embodiments, the ball of the valve 138 is biased towards the seat of the valve by a spring (not shown) extended from the lid 120. The seat of the valve 138 can be conically tapered to guide the ball into the seat and to facilitate formation of a positive seal when stopping flow of fluid from the pumping chamber to the organ chamber 192.

The base 132 is coupled to the lid 120. In some embodiments, a rim 139 of the base 132 and a rim 121 of the lid 120 are coupled together, e.g., about a perimeter of the pumping chamber. The base 132 and the lid 120 can be coupled using any suitable mechanism for coupling including, but not limited to, a plurality of screws, an adhesive, a glue, a weld, another suitable coupling mechanism, or any combination of the foregoing. A gasket 148 is disposed between the base 132 and the lid 120. The gasket 148 is configured to seal an engagement of the base 132 and the lid 120 to substantially prevent fluid in the pumping chamber from leaking therebetween. In some embodiments, the gasket 148 is an O-ring.

The base 132 defines a lumen 135 configured to be in fluid communication with a lumen 174 of an organ adapter 170, described in more detail below. The base 132 is configured to permit oxygenated perfusate to move from the pumping chamber through its lumen 135 into the lumen 174 of the organ adapter 170 towards the organ chamber 192. In this manner, the lumen 135 of the base 132 is configured to help fluidically couple the pumping chamber and the organ chamber 192.

The organ adapter 170 is configured to substantially retain the bodily tissue with respect to the apparatus 100. The organ adapter 170 can be similar in many respects to an adapter described herein (e.g., adapter 26, described above, and/or adapter 770, described below). The organ adapter 170 includes a handle portion 178, an upper portion 172, and a protrusion 180, and defines the lumen 174 extended there through. The upper portion 172 of the organ adapter 170 is extended from a first side of the handle portion 178. The protrusion 180 of the organ adapter 170 is extended from a second side of the handle portion 178 different than the first side of the handle portion. At least a portion of the protrusion 180 is configured to be inserted into the bodily tissue. More specifically, at least a portion of the protrusion 180 is configured to be inserted into a vessel (e.g., an artery, a vein, or the like) of the bodily tissue. In some embodiments, the protrusion 180 is configured to be coupled to the bodily tissue via an intervening structure, such as silastic or other tubing.

As illustrated in FIG. 3, at least a portion of the protrusion 180 includes a series of tapered steps such that a distal end 181 of the protrusion is narrower than a proximal end 183 of the protrusion. In this manner, the protrusion 180 is configured to be inserted into a range of vessel sizes. For example, the protrusion 180 can be configured to be received in a bodily vessel, e.g., a heart vessel, shown in FIG. 2, having a diameter within the range of about 3 millimeters to about 8 millimeters. In this manner, the protrusion 180 is configured to deliver the fluid (e.g., the oxygenated perfusate) from the pumping chamber to the vessel of the bodily tissue via the lumen 174 defined by the organ adapter 170. The vessel of the bodily tissue can be sutured to the protrusion 180 of the adapter 170. As shown in FIG. 2, the perfusate may leave the organ via a second vessel and return to the organ chamber 192.

While not shown in FIGS. 2 and 3, the apparatus may additionally comprise one or more oxygen sensors to facilitate measuring oxygen concentrations in the perfusate prior to entering the organ and after leaving the organ. For example, an oxygen sensor may be placed in fluidic contact with the interior of organ adapter 170 such that the oxygen level of the perfusate is measured immediately prior to entering the organ. Additional sensors may be placed in organ chamber 192 to measure the oxygen level of the perfusate after it leaves the organ. Additional oxygen sensors may be placed throughout the lid or container as needed. In some instances, each oxygen sensor will be installed in duplicate to assure that the apparatus maintains continuous monitoring of oxygen levels. Using the measurements from the oxygen sensors, it is possible to determine an oxygen consumption rate for the organ, as described above.

In one embodiment, shown in FIG. 3, the organ adapter 170 includes a first arm 182 having a first end portion 185 and a second arm 184 having a second end portion 187. The first and second arms 182, 184 are configured to facilitate retention of the bodily tissue with respect to the organ adapter 170. A retention mechanism, (not shown) may configured to be attached, coupled, or otherwise disposed about each of the first and second arms 182, 184. The retention mechanism can be any suitable retention mechanism described above with respect to the apparatus 10, including, for example, a net, a cage, a sling, or the like. A middle portion of the retention mechanism is configured to be disposed about at least a portion of the bodily tissue coupled to the protrusion 180 of the adapter 170. End portions of the retention mechanism are configured to be disposed about each of the first and second arms 182, 184 of the organ adapter 170. The first end portion 185 of the first arm 182 and the second end portion 187 of the second arm 184 are each configured to facilitate retention of the end portions of the retention mechanism with respect to the first and second arms, respectively. For example, as shown in FIG. 3, each of the first and second end portions 185, 187 of the first and second arms 182, 184, respectively, defines a shoulder portion configured to help prevent the end portions of the retention mechanism from being inadvertently removed from the first or second arm, respectively.

The upper portion 172 of the organ adapter 170 is configured to couple the organ adapter to the base 132. The upper portion 172 of the organ adapter is configured to be received by the lumen 135 defined by the base. The upper portion 172 includes a first projection 176 and a second projection (not shown) spaced apart from the first projection. The projections 176 of the organ adapter 170 are configured to be received by the lumen 135 of the base 132 in opposing spaces between a first protrusion 154 and a second protrusion 156 disposed within the lumen of the base. Once the upper portion 172 is received in the lumen 135 of the base 132, the organ adapter 170 can be rotated approximately ninety degrees such that its first projection 176 and its second projection sit on a shoulder 155, 157 defined by the protrusions 154, 156 of the base, respectively. The organ adapter 170 can be rotated in either a clockwise or a counterclockwise direction to align its projections with the shoulders of the protrusions of the base 132. Similarly, the organ adapter 170 can be rotated in either the clockwise or the counterclockwise direction to unalign its projections with the shoulders of the protrusions of the base 132, such as for decoupling of the adapter from the base. Said another way, the organ adapter 170 can be configured to be coupled to the base 132 with a bayonet joint. The handle portion 178 is configured to facilitate coupling and decoupling of the organ adapter 170 and the base 132. For example, the handle portion 178 is configured to be grasped by a hand of an operator of the apparatus 100. As shown in FIG. 3, the handle portion 178 is substantially disc-shaped, and includes a series of recesses configured to facilitate grasping the handle portion with the operator's hand.

A gasket 188 is disposed about the upper portion 172 of the organ adapter 170 between the handle portion 178 of the adapter and the base 132. The gasket 188 is configured to substantially prevent a fluid from flowing between the pumping chamber and the organ chamber 192 within a channel formed between an outer surface of the upper portion 172 of the organ adapter 170 and an inner surface of the lumen 135 of the base 132. In some embodiments, the gasket 188 is compressed between the organ adapter 170 and the base 132 when the organ adapter is coupled to the base.

In some embodiments, at least a portion of the lid assembly 110 is configured to minimize flexure of the portion of the lid assembly, such as may occur in the presence of a positive pressure (or pulse wave) caused by introduction of oxygen into the pumping chamber and/or of oxygenated perfusate into the organ chamber 192. For example, as illustrated in FIG. 3, the upper portion 122 of the lid 120 includes a plurality of ribs 126 configured to minimize flexure of the lid 120 when oxygen is pumped through the pumping chamber. In other words, the plurality of ribs 126 structurally reinforces the lid 120 to help prevent the lid 120 from flexing. The plurality of ribs 126 are extended from a top surface of the lid 120 in a substantially parallel configuration. In another example, the lower portion 128 of the lid 120 can include a plurality of ribs (not shown) configured to reinforce the top of the pumping chamber to help prevent flexure of the top of the pumping chamber during pumping of oxygen through the lid assembly 110. In yet another example, the base 132 is configured to substantially minimize flexure of the base, such as may occur in the presence of a positive pressure caused by the introduction of oxygen into the pumping chamber and/or of oxygenated perfusate into the organ chamber 192. As illustrated in FIG. 3, the base 132 includes a plurality of ribs 131 extended from its upper surface 134. Each of the plurality of ribs 131, 133 is configured to reinforce the base 132, which helps to minimize flexure of the base.

The lid assembly 110 includes a fill port 108 configured to permit introduction of a fluid (e.g., the perfusate) into the organ chamber 192 (e.g., when the lid assembly is coupled to the canister 190). The fill port 108 can be similar in many respects another port described herein (e.g., port 34, described above, and/or port 708, described below). In the embodiment illustrated in FIG. 2 and FIG. 3, the fill port 108 is formed by a fitting 107 coupled to the lid 120 and that defines a lumen 109 in fluidic communication with a lumen 143 in the first gasket 142, which lumen 143 is in fluidic communication with a lumen 137 defined by the base 132, which lumen 137 is in fluidic communication with the organ chamber 192. The fitting 107 can be any suitable fitting, including, but not limited to, a luer lock fitting. The fill port 108 can include a cap (not shown) removably coupled to the port via a retaining strap. The cap can help prevent inadvertent movement of fluid, contaminants, or the like through the fill port 108.

The lid assembly 110 is configured to be coupled to the canister 190. The canister 190 can be similar in many respects to a canister described herein (e.g., canister 32, described above, and/or canister 390, 790, 990, described below). The canister includes a wall 191, a floor 193, and a compartment 194 defined on its sides by the wall and on its bottom by the floor. The compartment 194 can form a substantial portion of the organ chamber 192. As shown in FIG. 3, at least a portion of the lid assembly 110 (e.g., the base 132) is configured to be received in the compartment 194 of the canister 190. A gasket 152 is disposed between the base 132 and an inner surface of the wall 191 of the canister 190. The gasket 152 is configured to seal the opening between the base 132 and the wall 191 of the canister 190 to substantially prevent flow of fluid (e.g., the perfusate) there through. The gasket 152 can be any suitable gasket, including, for example, an 0-ring. In some embodiments, the canister 190 includes a port 196 disposed on the wall 191 of the canister.

The floor 193 of the canister 190, shown in FIG. 2, is configured to flex when a first pressure within the organ chamber 192 changes to a second pressure within the organ chamber, the second pressure different than the first pressure. More specifically, in some embodiments, the floor 193 of the canister 190 is configured to flex when a first pressure within the organ chamber 192 is increased to a second pressure greater than the first pressure. For example, the floor 193 of the canister 190 can be configured to flex in the presence of a positive pressure (or a pulse wave) generated by the pumping of the oxygenated perfusate from the pumping chamber into the organ chamber 192, as described in more detail below. In some embodiments, the floor 193 of the canister 190 is constructed of a flexible membrane. The floor 193 of the canister 190 can have any suitable thickness. For example, in some embodiments, the floor 193 of the canister 190 has a thickness of about 0.075 to about 0.085 inches. In some embodiments, the floor 193 of the canister 190 is about 0.080 inches thick.

The canister 190 can be configured to enable an operator of the apparatus 100 to view the bodily tissue when the bodily tissue is sealed within the organ chamber 192. In some embodiments, for example, at least a portion of the canister 190 (e.g., the wall 191) is constructed of a transparent material. In another example, in some embodiments, at least a portion of the canister 190 (e.g., the wall 191) is constructed of a translucent material. In some embodiments, the canister 190 includes a window (not shown) through which at least a portion of the organ chamber 192 can be viewed.

Figure 4:
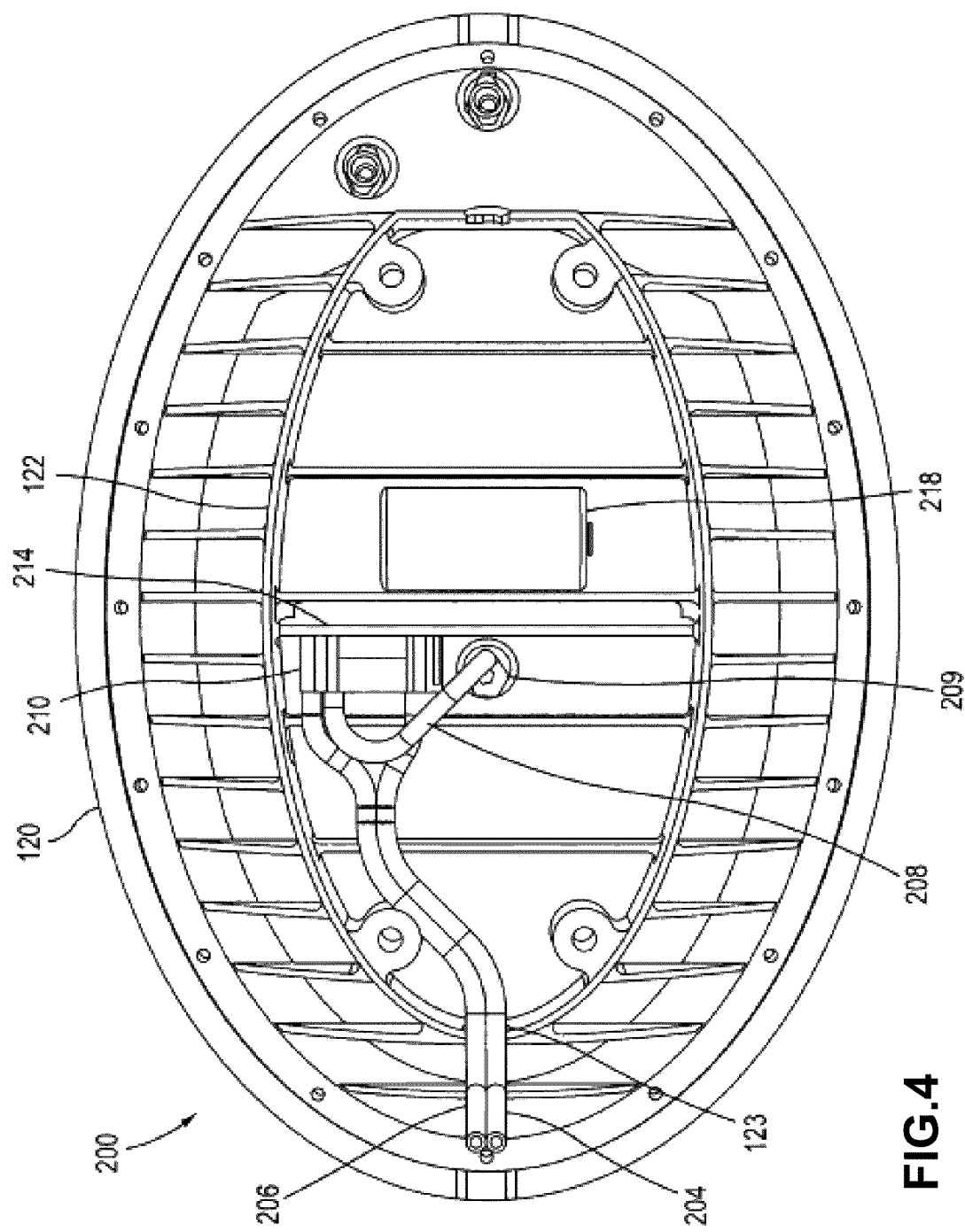
FIG. 4 is a diagram of a pneumatic system suitable for use with an embodiment of the invention.

As noted above, the apparatus 100 is configured for controlled delivery of fluid (e.g., oxygen) from an external source (not shown) into the pumping chamber of the lid assembly 110. The external source can be, for example, an oxygen cylinder. In some embodiments, e.g. as shown in FIG. 4, the pneumatic system 200 is configured for controlled venting of fluid (e.g., carbon dioxide) from the pumping chamber to an area external to the apparatus 100 (e.g., to the atmosphere). The pneumatic system 200 is moveable between a first configuration in which the pneumatic system is delivering fluid to the pumping chamber and a second configuration in which the pneumatic system is venting fluid from the pumping chamber. The pneumatic system 200 includes a supply line 204, a vent line 206, a control line 208, a valve 210, a printed circuit board assembly ("PCBA") 214, and a power source 218.

The supply line 204 is configured to transmit fluid from the external source to the valve 210. A first end of the supply line 204 external to the lid 120 is configured to be coupled to the external source. A second end of the supply line 204 is configured to be coupled to the valve 210. Referring to FIG. 3, a portion of the supply line 204 between its first end and its second end is configured to be extended from an area external to the lid 120 through an opening 123 defined by the lid into the chamber 124 defined by the lid. In some embodiments, the supply line 204 is configured to transmit fluid to the valve 210 at a pressure of about 2 pounds per square inch ("p.s.i."), plus or minus ten percent.

The vent line 206 is configured to transmit fluid (e.g., oxygen, carbon dioxide) from the valve 210 to an area external to the chamber 124 of the lid 120. A first end of the vent line 206 is configured to be coupled to the valve 210. In some embodiments, the second end of the vent line 206 is a free end such that the fluid is released into the atmosphere. A portion of the vent line 206 between its first end and its second end is configured to be extended from the valve 210 through the chamber 124 and the opening 123 defined by the lid 120 to the area external to the lid.

As shown in FIG. 4, the control line 208 is configured to transmit fluid between the valve 210 and the pumping chamber of the lid assembly 110. A first end of the control line 208 is coupled to the valve 210. A second end of the control line 208 is coupled to the pumping chamber. In some embodiments, the control line 208 is mechanically and fluidically coupled to the pumping chamber by an adapter 209. The adapter 209 can be any suitable mechanism for coupling the control line 208 to the pumping chamber. In some embodiments, for example, the adapter 209 includes a male fitting on a first end of the adapter that is configured to be disposed in the second end of the control line 208 and threaded portion on a second end of the adapter configured to be received in a correspondingly threaded opening in the lower portion 128 of the lid 120. When the pneumatic system 200 is in its first configuration, the control line 208 is configured to transmit fluid from the supply line 204 via the valve 210 to the pumping chamber. When the pneumatic system 200 is in its second configuration, the control line 208 is configured to transmit fluid from the pumping chamber to the vent line 206 via the valve 210. Each of the foregoing lines (i.e., supply line 204, vent line 206, control line 208) can be constructed of any suitable material including, for example, polyurethane tubing.

The valve 210 is configured to control the flow of oxygen into and out of the pumping chamber. In the embodiment illustrated in FIG. 4, the valve 210 is in fluidic communication with each of the supply line 204, the vent line 206, and the control line 208 via a first port, a second port, and a third port (none of which are shown in FIG. 4), respectively. In this manner, the valve 210 is configured to receive the fluid from the supply line 204 via the first port. In some embodiments, the first port defines an orifice that is about 0.10 to about 0.60 mm in size. In other embodiments, the first port defines an orifice that is about 0.15 to about 0.50 mm in size, about 0.20 to about 0.40 mm in size, about 0.20 to about 0.30 mm in size, or about 0.25 to about 0.30 mm in size. Specifically, in some embodiments, the first port defines an orifice that is about 0.25 mm in size. The valve 210 is configured to deliver the fluid to the vent line 206 via the second port. Additionally, the valve 210 is configured to receive the fluid from and deliver the fluid to the control line 208 via the third port. Specifically, the valve 210 is movable between a first configuration and a second configuration. In its first configuration, the valve 210 is configured to permit the flow of fluid from the supply line 204 through the valve 210 to the control line 208. As such, when the valve 210 is in its first configuration, the pneumatic system 200 is in its first configuration. In its second configuration, the valve 210 is configured to permit the flow of fluid from the control line 208 through the valve to the vent line 206. As such, when the valve 210 is in its second configuration, the pneumatic system 200 is in its second configuration.

The valve 210 is in electrical communication with the power source 218. In some embodiments, for example, the valve 210 is in electrical communication with the power source 218 via the PCBA 214. In the embodiment illustrated in FIGS. 3 and 4, the PCBA 214 is disposed in the chamber 124 between the valve 210 and the power source 218. In some embodiments, the PCBA 214 includes an electrical circuit (not shown) configured to electrically couple the power source 218 to the valve 210. The power source 218 is configured to provide power to the valve 210 to enable the valve 210 to control the flow of oxygen. In some embodiments, the power source 218 is configured to provide power to the valve 210 to enable the valve to move between its first configuration and its second configuration. The power source can be any suitable source of power including, for example, a battery. More specifically, in some embodiments, the power source is a lithium battery (e.g., a Li/MnO$_2$ 2/3A battery). In another example, the power source can be an AA, C or D cell battery.

The valve 210 can be any suitable mechanism for controlling movement of the fluid between the first port, the second port, and the third port (and thus the supply line 204, vent line 206, and the control line 208, respectively). For example, in the embodiment illustrated in FIG. 4, the valve 210 is a solenoid valve. As such, in operation, the valve 210 is configured to convert an electrical energy received from the power source 218 to a mechanical energy for controlling the flow of oxygen therein. In some embodiments, for example, the valve 210 is configured to move to its first configuration when power is received by the valve from the power source 218. In some embodiments, the valve 210 is configured to move to its second configuration when the valve is electrically isolated (i.e., no longer receiving power) from the power source 218. In other words, the valve 210 is configured to deliver fluid (e.g., oxygen) to the pumping chamber when the solenoid of the valve is energized by the power source 218, and the valve is configured to vent fluid (e.g., oxygen, carbon dioxide) from the pumping chamber when the solenoid of the valve is not energized by the power source. In some embodiments, the valve 210 is biased towards its second (or venting) configuration (in which power is not being provided from the power source 218 to the valve). Because the power source 218 is configured to not be in use when the pneumatic system 200 is not delivering oxygen to the pumping chamber, the usable life of the power source is extended, which enables the organ to be extracorporeally preserved within the apparatus 100 for a longer period of time. For example, in some embodiments, the solenoid of the valve 210 is configured to receive power from the power source 218 for about 20 percent of the total time the apparatus 100, or at least the pneumatic system 200 of the apparatus, is in use.

In some embodiments, the flow of fluid from the supply line 204 to the valve 210 is substantially prevented when the valve is in its second configuration. In this manner, the flow of oxygen into the valve 210 from the supply line 204 is stopped while the valve is venting fluid from the pumping chamber. As such, the overall oxygen use of the apparatus 100 is reduced. In other embodiments, when the valve 210 is in its second configuration, the fluid being transmitted into the valve from the supply line 204 is transmitted through the valve to the vent line 206 without entering the pumping chamber. In this manner, the inflow of fluid from the supply line 204 to the valve 210 is substantially continuous. Accordingly, the flow of fluid from the valve 210 to the vent line 206 is also substantially continuous because the valve 210 is substantially continuously venting fluid from at least one of the supply line 204 and/or the control line 208.

Figure 5:
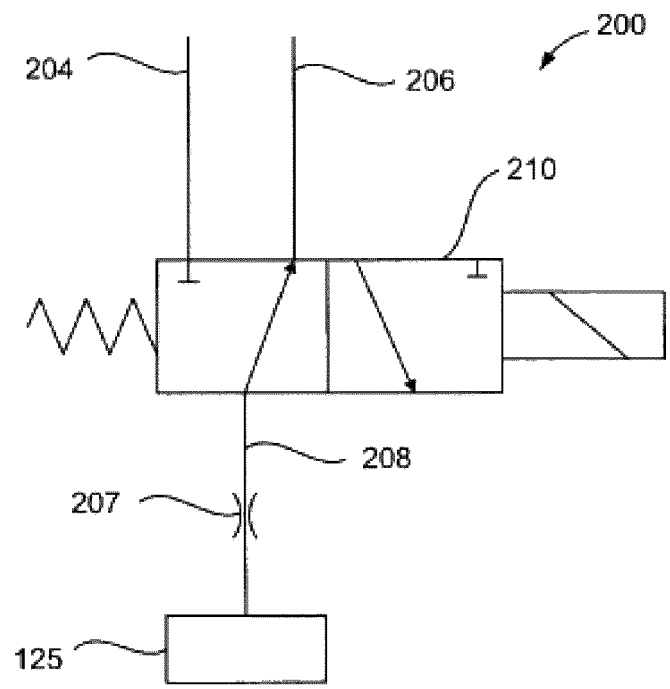
FIG. 5 is schematic drawing of a flow system suitable for use with an embodiment of the invention.

Referring to a schematic illustration of the pneumatic system and pumping chamber in FIG. 5, the pneumatic system 200 is configured to control a change in pressure within the pumping chamber of the lid assembly 110. In some embodiments, the pneumatic system 200 is configured to control the pressure within the pumping chamber via the control line 208. More specifically, the rate of flow of fluid between the valve 210 and the pumping chamber via the control line 208 is determined by a control orifice 207 disposed within the control line. The control orifice 207 can be, for example, a needle valve disposed within the control line 208. In some embodiments, the control orifice is about 0.10 to about 0.60 mm in size. In other embodiments, the first port defines an orifice that is about 0.15 to about 0.50 mm in size, about 0.20 to about 0.40 mm in size, about 0.20 to about 0.30 mm in size, or about 0.25 to about 0.30 mm in size. For example, in some embodiments, the control orifice 207 is about 0.25 mm in size. Because the rate of a change (e.g., rise, fall) in pressure within the pumping chamber is based on the rate of flow of the fluid between the valve 210 and the pumping chamber via the control line 208, the pressure within the pumping chamber is also determined by the size of the control orifice 207 in the control line 208.

The pneumatic system 200 can be configured to move between its first configuration and its second configuration based on a predetermined control scheme. In some embodiments, the pneumatic system 200 is configured to move between its first configuration and its second configuration on a time-based control scheme. In some embodiments, the pneumatic system 200 is configured to move from its first configuration to its second configuration after a first period of time has elapsed. For example, the pneumatic system 200 can be configured to move from its first configuration to its second configuration after about 170 milliseconds. As such, the pneumatic system 200 is configured to deliver fluid (e.g., oxygen) to the pumping chamber for the first time period (e.g., about 170 milliseconds). The pneumatic system 200 is configured to move from its second configuration to its first configuration after a second period of time has elapsed. For example, the pneumatic system 200 can be configured to move from its second configuration to its first configuration after being in its second configuration for about 700 milliseconds. As such, the pneumatic system 200 is configured to vent fluid (e.g. carbon dioxide) from the pumping chamber for the second time period (e.g., about 700 milliseconds). The pneumatic system 200 is configured to alternate between its first configuration and its second configuration, and thus between delivering fluid into the pumping chamber and venting fluid from the pumping chamber.

Although the pneumatic system 200 has been illustrated and described above as having a time-based control scheme, in some embodiments, the pneumatic system 200 is configured to move between its first configuration and its second configuration on a pressure-based control scheme. In some embodiments, the pneumatic system 200 is configured to move from its first configuration to its second configuration when a pressure within the pumping chamber reaches a first threshold pressure. For example, the pneumatic system 200 can be configured to move from its first configuration to its second configuration when the pressure within the pumping chamber is about 20 mmHg (millimeters of mercury), about 25 mmHg, about 30 mmHg, about 35 mmHg, about 40 mmHg, about 45 mmHg or about 50 mmHg. The pneumatic system 200 can be configured to move from its second configuration to its first configuration when a pressure within the pumping chamber reaches a second threshold pressure. For example, the pneumatic system 200 can be configured to move from its second configuration to its first configuration when the pressure within the pumping chamber is about 0 mmHg, about 5 mmHg, about 10 mmHg or about 15 mmHg. Said another way, when the pressure within the pumping chamber is increased from the second threshold pressure to the first threshold pressure, the valve 210 is switched from delivering fluid to the pumping chamber to venting fluid from the pumping chamber. Similarly, when the pressure within the pumping chamber is decreased from the first threshold pressure to the second threshold pressure, the valve 210 is switched from venting fluid from the pumping chamber to delivering fluid to the pumping chamber.

Because the pneumatic system 200 is configured to alternate between its first configuration and its second configuration, the pneumatic system 200 can be characterized as being configured to deliver oxygen to the pumping chamber via a series of intermittent pulses. In some embodiments, however, the pneumatic system 200 is configured to deliver oxygen to the pumping chamber in a substantially constant flow. In still another example, the pneumatic system 200 can be configured to selectively deliver oxygen in each of a substantially constant flow and a series of intermittent pulses. In some embodiments, the pneumatic system 200 is configured to control the flow of fluid within the pumping chamber, including the delivery of oxygen to the pumping chamber, in any combination of the foregoing control schemes, as desired by an operator of the apparatus 100.

Figure 6:
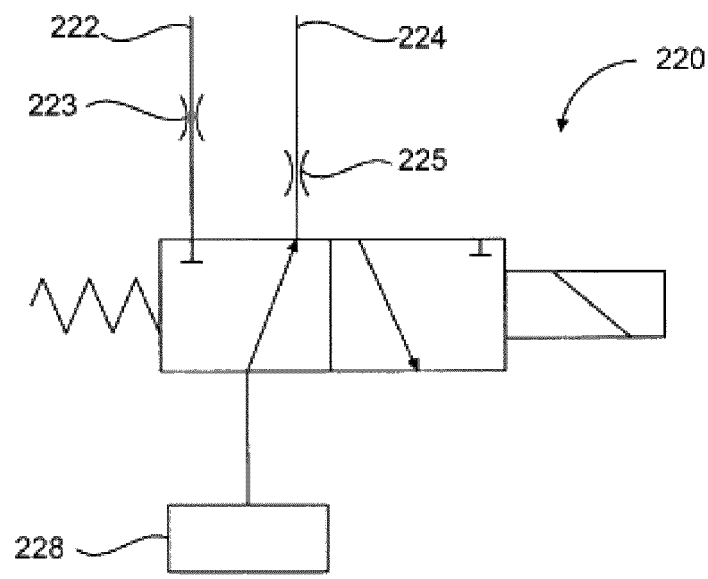
FIG. 6 is schematic drawing of a flow system suitable for use with an embodiment of the invention.

Although the pneumatic system 200 has been illustrated and described herein as controlling the change in pressure within the pumping chamber via a control orifice disposed in the control line 208, in other embodiments, a pneumatic system is configured to control the pressure within the pumping chamber via at least one control orifice disposed within at least one of the supply line and the vent line. As shown in FIG. 6, in some embodiments of a pneumatic system 220, a larger control orifice 223 is disposed within the supply line 222. In this manner, the pneumatic system 220 can permit a larger and/or quicker inflow of fluid from the supply line 222 to the pumping chamber, and thus can cause a quick pressure rise within the pumping chamber 228. In another example, in some embodiments, a smaller control orifice 225 is disposed within the vent line 224. In this manner, the pneumatic system 220 can restrict the flow of fluid venting through the vent line 224 from the pumping chamber 228, and thus can cause a slower or more gradual decline in pressure within the pumping chamber. As compared to pneumatic system 200, pneumatic system 220 can permit a shorter time period when the valve 210 is energized, thereby allowing power source 218 to operate the apparatus for a longer period.

In use, the bodily tissue is coupled to the organ adapter 170. The lid assembly 110 is disposed on the canister 190 such that the bodily tissue is received in the organ chamber 192. The lid assembly 110 is coupled to the canister 190. Optionally, the lid assembly 110 and the canister 190 are coupled via the clamp 250. A desired amount of perfusate is delivered to the organ chamber 192 via the fill port 108. Optionally, a desired amount of perfusate can be disposed within the compartment 194 of the canister 190 prior to disposing the lid assembly 110 on the canister. In some embodiments, a volume of perfusate greater than a volume of the organ chamber 192 is delivered to the organ chamber such that the perfusate will move through the ball check valve 138 into the second portion 129 of the pumping chamber.

A desired control scheme of the pneumatic system 200 is selected. Oxygen is introduced into the first portion 127 of the pumping chamber via the pneumatic system 200 based on the selected control scheme. The pneumatic system 200 is configured to generate a positive pressure by the introduction of oxygen into the first portion 127 of the pumping chamber. The positive pressure helps to facilitate diffusion of the oxygen through the membrane 140. The oxygen is diffused through the membrane 140 into the perfusate disposed in the second portion 129 of the pumping chamber, thereby oxygenating the perfusate. Because the oxygen will expand to fill the first portion 127 of the pumping chamber, substantially all of an upper surface 141 of the membrane 140 which faces the first portion of the pumping chamber can be used to diffuse the oxygen from the first portion into the second portion 129 of the pumping chamber.

As the organ uses the oxygen, the organ will release carbon dioxide into the perfusate. In some embodiments, the carbon dioxide is displaced from the perfusate, such as when the pneumatic system 200 the oxygen is diffused into the perfusate because of the positive pressure generated by the pneumatic system. Such carbon dioxide can be diffused from the second portion 129 of the pumping chamber into the first portion 127 of the pumping chamber. Carbon dioxide within the first portion 127 of the pumping chamber is vented via the control line 208 to the valve 210, and from the valve through the vent line 206 to the atmosphere external to the apparatus 100.

The positive pressure also causes the membrane 140 to flex, which transfers the positive pressure in the form of a pulse wave into the oxygenated perfusate. The pulse wave generated by the pumping chamber is configured to facilitate movement of the oxygenated perfusate from the second portion 129 of the pumping chamber into the bodily tissue via the organ adapter 170, thus perfusing the bodily tissue. In some embodiments, the pumping chamber is configured to generate a pulse wave that is an about 60 Hz pulse. In some embodiments, the pumping chamber is configured to generate a pulse wave through the perfusate that is configured to cause a differential pressure within the organ chamber 192 to be within the range of about 0 mmHg to about 50.0 mmHg. More specifically, in some embodiments, the pumping chamber is configured to generate a pulse wave through the perfusate that is configured to cause a differential pressure within the organ chamber 192 to be within the range of about 5 mmHg to about 30.0 mmHg. In some embodiments, the pumping chamber is configured such that the mobile perfusion device varies a pressure on the perfusate, e.g., an oxygenated solution, at least once per minute.

At least a portion of the perfusate perfused through the organ is received in the organ chamber 192. In some embodiments, the pulse wave is configured to flow through the perfusate disposed in the organ chamber 192 towards the floor 193 of the canister 190. The floor 193 of the canister 190 is configured to flex when engaged by the pulse wave. The floor 193 of the canister 190 is configured to return the pulse wave through the perfusate towards the top of the organ chamber 192 as the floor 193 of the canister 190 is returned towards its original non-flexed position. In some embodiments, the returned pulse wave is configured to generate a sufficient pressure to open the ball check valve 138 disposed at the highest position in the organ chamber 192. In this manner, the returned pulse wave helps to move the valve 138 to its open configuration such that excess fluid (e.g., carbon dioxide released from the bodily tissue and/or the perfusate) can move through the valve from the organ chamber 192 to the pumping chamber.

The foregoing perfusion cycle can be repeated as desired. For example, in some embodiments, the pneumatic system 200 is configured to begin a perfusion cycle approximately every second based on a time-based control scheme. As such, the pneumatic system 200 is configured to power on to deliver oxygen to the pumping chamber for several milliseconds. The pneumatic system 200 can be configured to power off for several milliseconds, for example, until time has arrived to deliver a subsequent pulse of oxygen to the pumping chamber. Because the pneumatic system 200, and the solenoid valve 210 specifically, is only powered on when needed to transmit a pulse of oxygen to the pumping chamber, the usable life of the power source 218 can be extended for a longer period of time.

Figure 7:
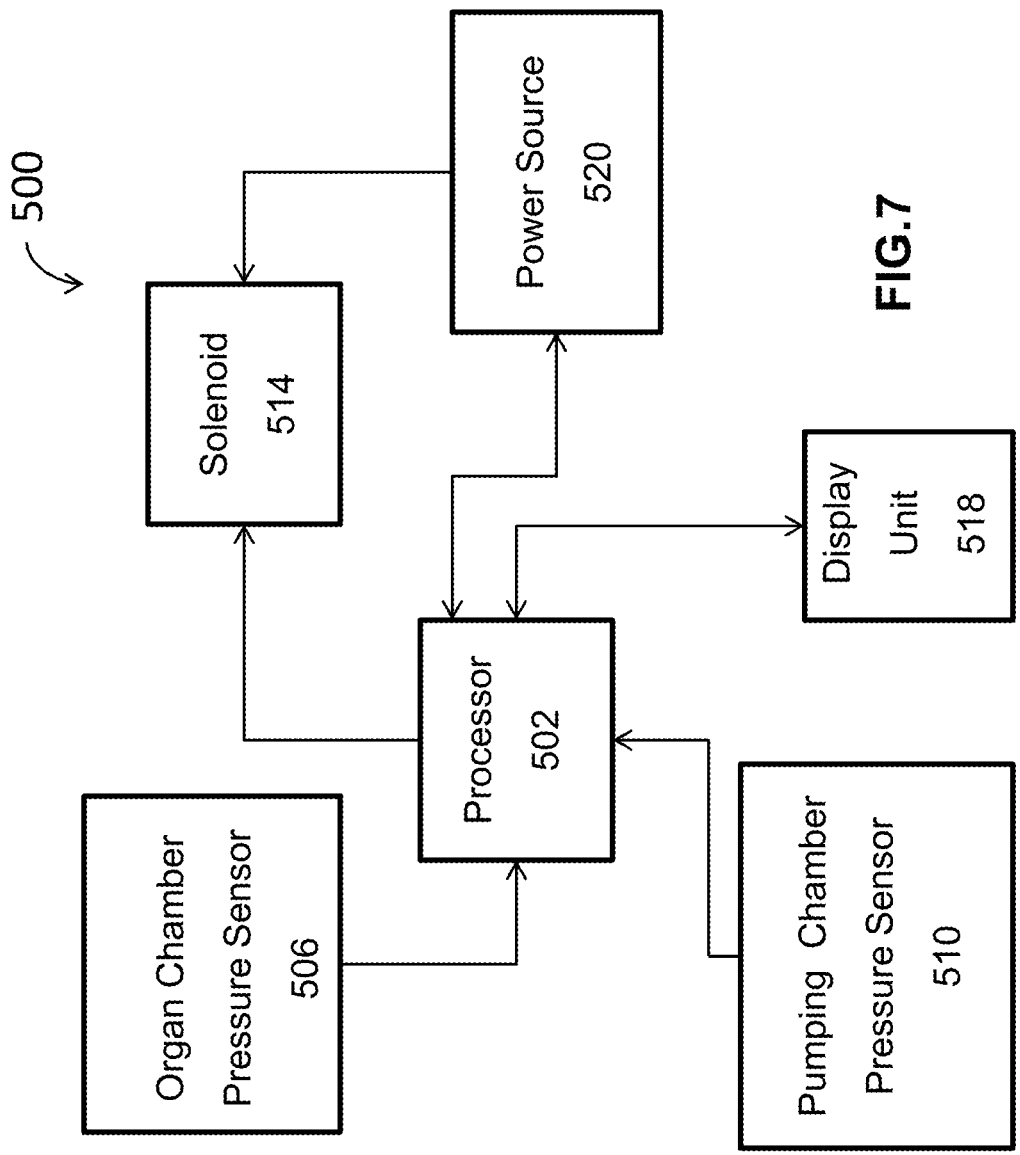
FIG. 7 is a flow diagram of a control system suitable for use with an embodiment of the invention.

Referring to FIG. 7, the control system 500 includes a processor 502, an organ chamber pressure sensor 506, a pumping chamber pressure sensor 510, a solenoid 514, a display unit 518, and a power source 520. In some embodiments, the control system 500 includes additional components, such as, for example, components configured for wired or wireless network connectivity (not shown) for the processor 502.

The control system 500 is described herein with reference to the apparatus 100, however, the control system is suitable for use with other embodiments described herein (e.g., apparatus 10 or 700). The pumping chamber pressure sensor 510 is configured to detect the oxygen pressure in the pumping chamber 125. Because the pumping chamber 125 is split into the first and second portions 127, 129, respectively, by the semi-permeable membrane 140, which is configured to undergo relatively small deflections, the oxygen pressure in the first portion 127 of the pumping chamber 125 is approximately equal to the fluid (e.g., perfusate) pressure in the second portion 129 of the pumping chamber 125. Therefore, measuring the fluid pressure in either the first portion 127 or the second portion 129 of the pumping chamber 125 approximates the fluid pressure in the other of the first portion or the second portion of the pumping chamber 125.

The organ chamber pressure sensor 506 is configured to detect the fluid pressure in the canister 190. Each pressure sensor 506, 510 can be configured to detect the fluid pressure in real-time and permit instantaneous determination of small pressure changes. Examples of pressure sensors that can be used include, but are not limited to, analog pressure sensors available from Freescale (e.g., MPXV5010GP-NDD) and from Honeywell (e.g., HSCMRNNOO1PGAA5). At least one of the pressure sensors 506, 510 can be configured to measure pressures between 0-1.0 psig with a 5 volt power supply. In some embodiments, at least one of the pressure sensors 506, 510 can be configured to detect pressure variations as small as 0.06 mmHg The sensors 506, 510 can be placed in the chamber 324 at the same height to avoid pressure head measurement errors.

The solenoid 514 is disposed in the chamber 124. The solenoid 514 is configured to control the opening and/or closing of one or more valves (not shown in FIG. 17) for gas flow to and from the pumping chamber 125. The solenoid 514 is operably connected to the power source 520 for optimal power management.

The display unit 518 is configured to display one or more parameters. Display parameters of the display unit 518 can include, for example, elapsed time of operation, operating temperature, organ flow rate, and/or organ resistance, which are key metrics for determining the overall health of the organ being transported by the apparatus 100. Calculation of the organ flow rate and the organ resistance parameters are described in more detail below. The processor 502 is configured to receive information associated with the oxygen pressure in the pumping chamber 125 and in the canister 190 via the sensors 510, 506, respectively. The processor 502 is configured to control operation of the solenoid 514, to control the supply of power from the power source 520 to the solenoid 514, and to display operating parameters on the display unit 518. In some embodiments, the processor 502 additionally receives information from the OCR Processor 680 (shown in FIG. 9) which communicates a measurement of the oxygen consumption rate of the organ. In these embodiments, the processor 502 may instruct solenoid 514 to open for longer to allow greater partial pressure of oxygen or increase the flow rate (discussed below).

Figure 8:
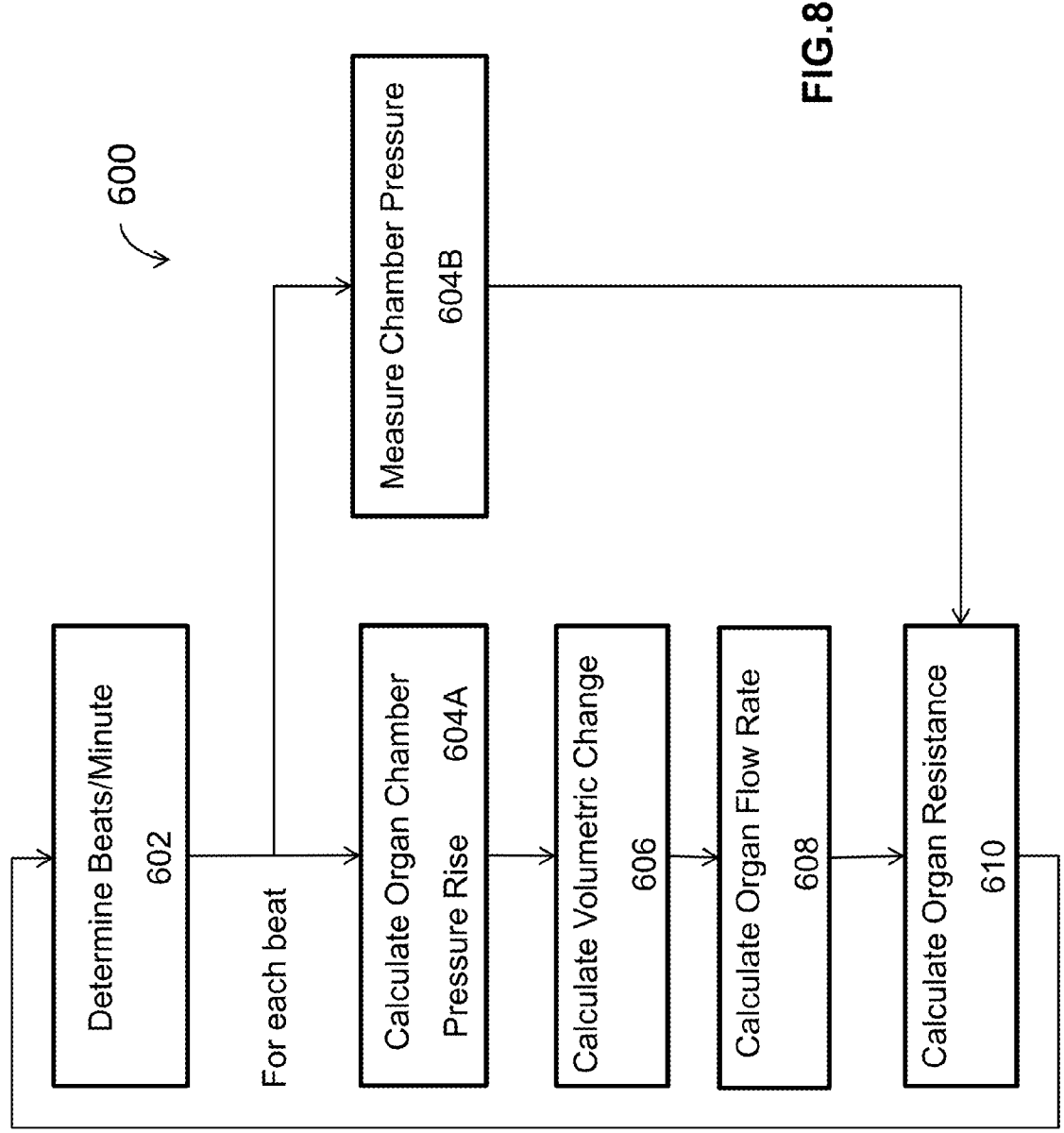
FIG. 8 is a flow diagram of a method for calculating organ flow rate and organ resistance according to an embodiment.

The processor 502 is configured to calculate the organ flow rate and the organ resistance, as illustrated in FIG. 8. Organ flow rate is a measure of the organ's compliance to fluid flow therethrough (e.g. blood flow), and can be a significant indicator of organ viability. Organ resistance, on the other hand, is a measure of the organ's resistance to fluid flow therethrough, and is theoretically a function of the pressure drop across the organ. In some embodiments, the processor 502 is configured to evaluate such parameters (i.e., organ flow rate and/or organ resistance) continually and in real time. In some embodiments, the processor 502 is configured to periodically evaluate such parameters at predetermined time intervals.

Referring to FIG. 8, a flow chart of a method 600 for evaluating a parameter, such as organ flow rate and/or organ resistance, according to an embodiment is illustrated. The method 600 is described herein with respect to apparatus 100 and control unit 500, however, can be performed by another apparatus described herein. At 602, the number of beats/minute (bpm) is determined. As used herein, "beat" refers to a pressure increase caused by a first volume of fluid (e.g., oxygen from pneumatic system 200) being introduced (e.g., intermittently) into the pumping chamber 125, which in turn causes a pressure wave that in turn causes a second volume of fluid (e.g., oxygenated perfusate) to be pumped or otherwise transferred from the pumping chamber 125 towards the canister 190 and/or an organ contained in the canister 190. Determination of the bpm can be based on the frequency with which the solenoid 514 (under the control of processor 502) permits gas exchange via the control orifice.

Because the canister 190 is compliant (i.e., it has a flexible floor 193), the canister flexes with each "beat" and then returns to its starting position. As the canister 190 floor flexes, the canister accepts the second volume of fluid from the pumping chamber 125, via flow through the organ (e.g., through vasculature of the organ, which can be coupled to an organ adapter in fluid communication with the pumping chamber 125). The canister 190 floor 193 flexing and relaxing process can be repeated for each beat.

As the second volume of fluid enters the canister 190, pressure in the canister 190 (or more specifically, an organ chamber 192, illustrated in FIG. 2, defined by the canister 190 and the lid assembly 110) rises and causes the canister 190 floor 193 to flex. This rise is pressure is measured by the organ chamber pressure sensor 506. At 604A, the rise in organ chamber pressure is calculated as a difference between the highest organ chamber pressure and lowest organ chamber pressure for each beat. In some embodiments, the organ chamber pressure is sampled at a rate significantly higher than the number of beats/minute (e.g. at 1 kHz for 60 bpm), such that multiple organ chamber pressure measurements are taken prior to performing the calculation of organ chamber pressure rise at 604A. For example, in some embodiments, the organ chamber pressure is sampled at 610 Hz (i.e., 610 samples per second).

As described above, the floor 193 of the canister 190 is a thin plate configured to undergo small deformations, such that its deflection due to pressure/volume changes is linear and is a measure of the volumetric compliance (defined as volume displaced per unit pressure change) of the canister. In one embodiment, volumetric compliance of the canister 190 is known and preprogrammed into the processor 502. In another embodiment, the processor 502 is configured to calculate volumetric compliance in real-time. At 606, the volumetric change is calculated by multiplying the calculated rise in canister pressure with the known/estimated volumetric compliance of the canister 190.

At 608, the organ flow rate is calculated by dividing the calculated change in volume by the beat period (i.e., a time interval between consecutive beats, measured in units of time). An average of several consecutive values of organ flow rate or other calculated values can be displayed to minimize beat variations. For example, a moving average value can be displayed.

At 610, the organ resistance is calculated. Organ resistance is expressed in units of pressure over organ flow rate, for example, mmHg/(mL/min) Organ flow rate is calculated as described above. The organ resistance is calculated by the processor 502 based upon the calculated canister pressure rise, calculated at 604A, and a measured chamber pressure, at 604B. The calculated canister pressure rise and measured chamber pressure can be based on substantially simultaneous and relatively high rate sampling of the pressure on each side of the organ (i.e. at both the organ chamber sensor 506 and the pumping chamber sensor 510). In some embodiments, the sampling rate is significantly higher than the number of beats per minute. For example, the pressures at the sensors 506, 510 can be sampled 1,000 times per second (1 kHz). At the start of the beat, the pressure on each side of the organ is approximately the same. Thus, the pressure drop across the organ is zero. As the oxygen pressure in the pumping chamber 125 rises, the pressure in the canister 190 rises at a slower rate. As the fluid subsequently returns to the pumping chamber 125 from the canister 190, the two pressures drop to equilibrium. Thus, the pressure across the organ varies throughout each beat. For improved accuracy, pressure can be measured at a high rate and accumulated for each beat period. For example, the total pressure impulse for each beat can be integrated step-wise. In this manner, organ resistance is calculated at 610 Hz. Further averaging or other statistical analysis can be performed by the processor 502 to reduce error. Due to the low operating pressures of the apparatus, an organ's resistance to flow can be approximated by laminar flow, such that instantaneous flow rate is proportional to the instantaneous pressure drop. Calculations can be performed in real-time using direct pressure measurements.

Figure 9:
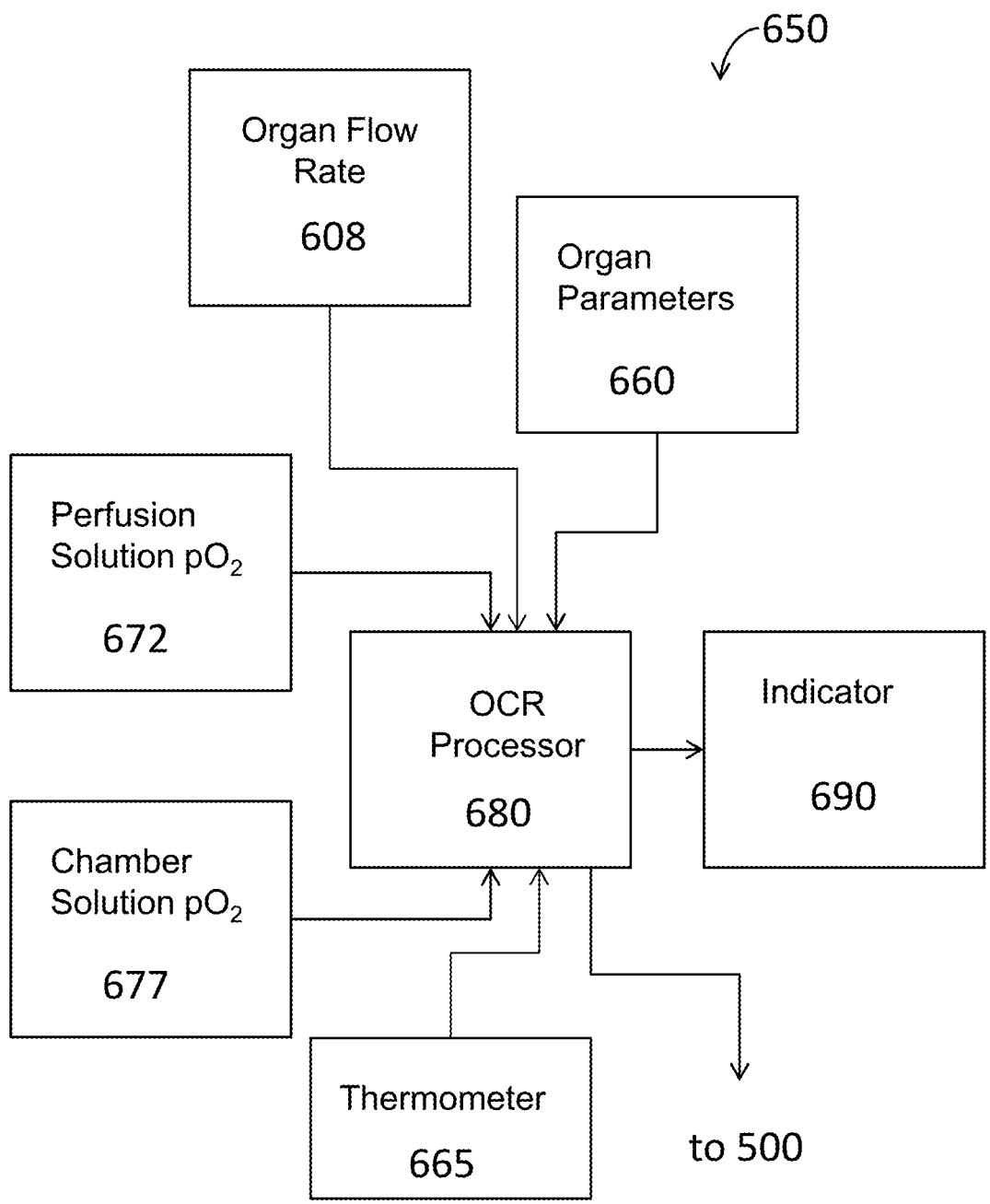
FIG. 9 is a flow diagram of a method for calculating the oxygen consumption rate of an organ.

A flow chart 650 describing the calculation of the oxygen consumption rate (OCR) and communication thereof to other systems of the apparatus is shown in FIG. 9. In the embodiment shown in FIG. 9, only two oxygen sensors are used, the first in communication with the perfusion solution (672) prior to entering the organ, e.g., in the pump chamber, and the second in communication with the chamber solution (677) after leaving the organ, e.g., in the organ chamber. The oxygen sensors 672 and 677 send their measurements to the OCR Processor 680, where an oxygen consumption rate is calculated using the methods discussed above, for example, based upon the measured organ flow rate 608 and the temperature of the perfusate measured by the thermometer 665. Additionally, because the apparatus may be used for multiple organs, it may be necessary to input organ parameters 660 which may include ranges of acceptable OCR values for an organ type or an organ of a given mass. The solubility constant for the perfusate may also be entered as needed to correspond to the perfusate used, for example, preservation solution. The calculated OCR value may be displayed via the indicator 690 or the OCR value can be compared to a range of "normal" OCR values and an alert (e.g., light or sound) generated when the calculated OCR is outside of the normal range.

In some embodiments, the OCR value may be communicated to the control system 500 in a feedback loop, allowing the apparatus to modify the temperature, pressure, flow rate, pressure cycle, or oxygenation based upon the OCR value. For example, in the event that the OCR had decreased to an amount outside of the "normal" range, the processor 502 may command that perfusate pressure is increased to encourage the organ to consume more oxygen. Alternatively, the processor 502 may allow the perfusate to warm, thereby increasing the respiration rate of the organ.

Another apparatus 700 suitable for use with the invention is illustrated in FIGS. 10-14. The apparatus 700 is configured to oxygenate a perfusate and to perfuse an organ for extracorporeal preservation of the organ. Unless stated otherwise, the apparatus 700 can be similar in many respects (e.g., form and/or function) to the other apparatus described herein (e.g., apparatus 10 or 100), and can include components similar in many respects (e.g., form and/or function) to components of the apparatus described herein. The apparatus 700 includes a lid assembly 710, a canister 790, and a coupling mechanism 850.

The lid assembly 710 defines a chamber 724 configured to receive components of a pneumatic system (not shown), such as the pneumatic system 200 described above, and/or a control system (not shown), such as the control system 500 described above. In some embodiments, the chamber 724 is formed by a lid 720 of the lid assembly 710. In some embodiments, the chamber 724 can be formed between a lower portion 723 of the lid 720 and an upper portion 722 of the lid.

Figure 10:
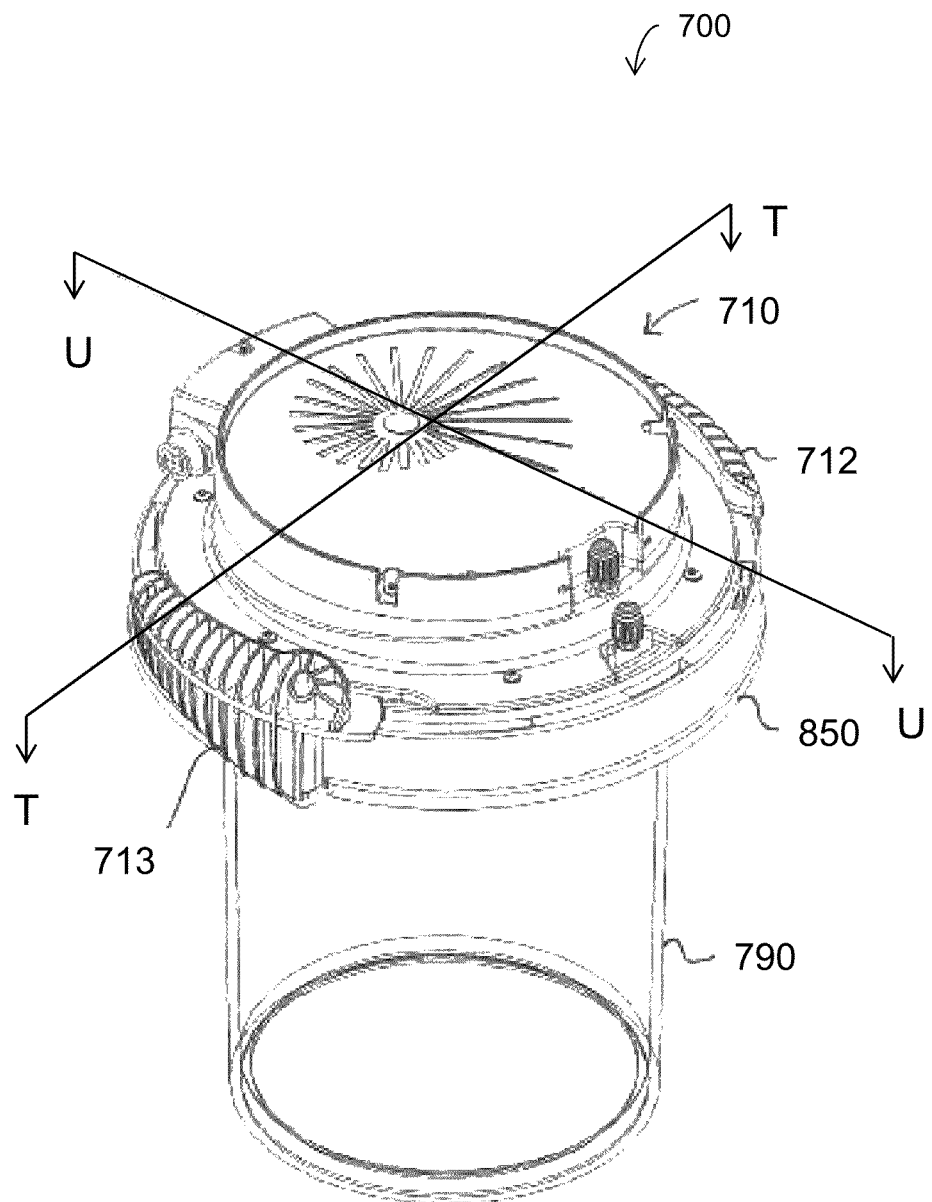
FIG. 10 is a diagram of an embodiment of a perfusion device for use with an embodiment of the invention.
Figure 11:
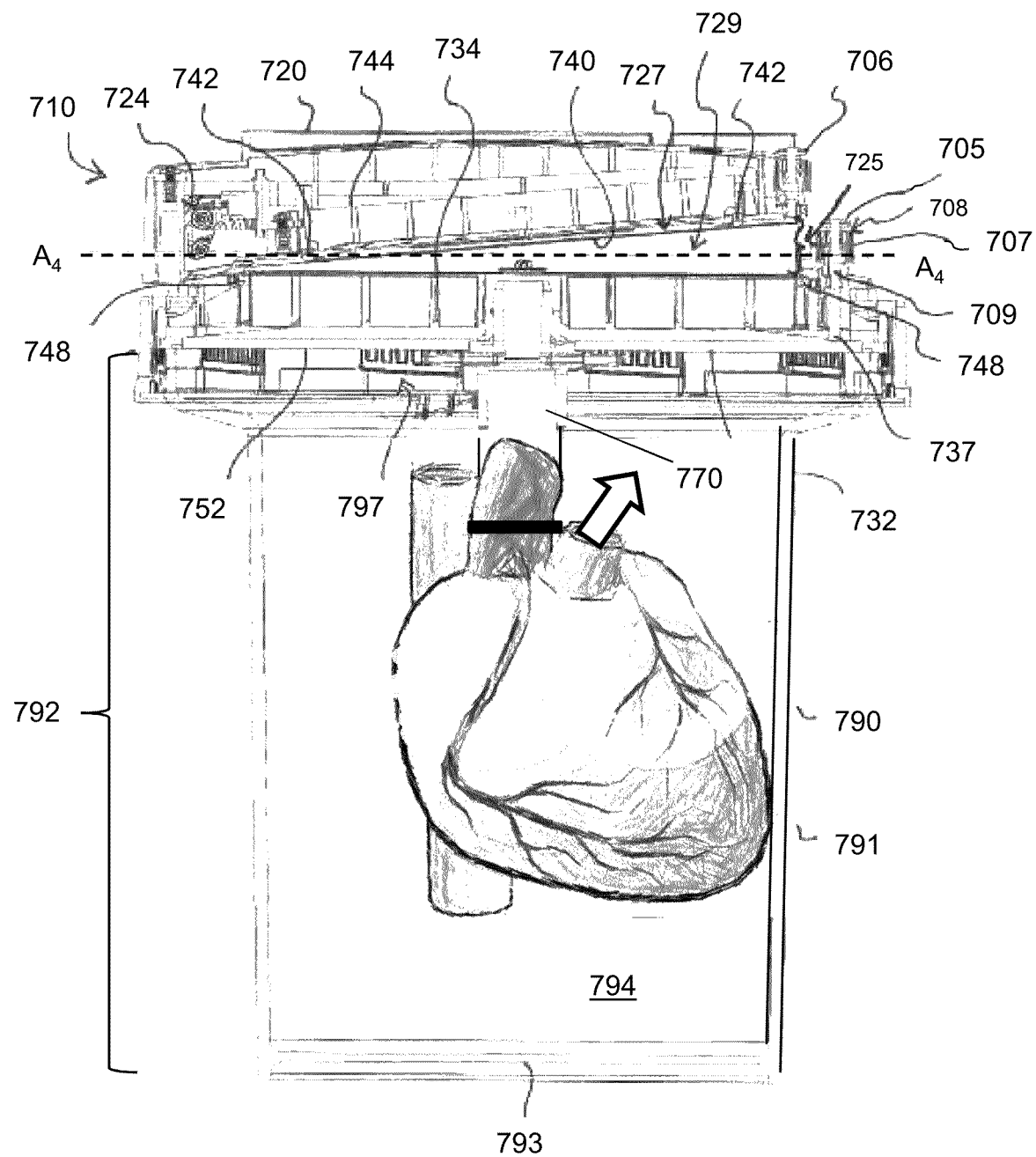
FIG. 11 is a diagram of an embodiment of a perfusion device for use with an embodiment of the invention.

As shown in FIGS. 10 and 11, the lid assembly 710 defines a pumping chamber 725 configured to receive oxygen (e.g., from the pneumatic system), to facilitate diffusion of the oxygen into a perfusate (not shown) and to facilitate movement of the oxygenated perfusate into an organ, e.g., a heart. A top of the pumping chamber 725 is formed by a lower portion 728 of a membrane frame 744 of the lid assembly 710. A bottom of the pumping chamber 725 is formed by an upper surface 734 of a base 732 of the lid assembly 710.

As illustrated in FIG. 11, the lid assembly 710 includes a first gasket 742, a membrane 740, and the membrane frame 744. The membrane 740 is disposed within the pumping chamber 725 and divides the pumping chamber 725 into a first portion 727 and a second portion 729 different than the first portion. The first gasket 742 is disposed between the membrane 740 and the membrane frame 744 such that the first gasket is engaged with an upper surface 741 of the membrane 740 and a lower, perimeter portion of the membrane frame 744. The first gasket 742 is configured to seal a perimeter of the first portion 727 of the pumping chamber 725 twinned between the lower portion 728 of the membrane frame 744 and the upper surface 741 of the membrane 740. In other words, the first gasket 742 is configured to substantially prevent lateral escape of oxygen from the first portion 727 of the pumping chamber 725 to a different portion of the pumping chamber. In the embodiment illustrated in FIG. 11, the first gasket 742 has a perimeter substantially similar in shape to a perimeter defined by the membrane 740 (e.g., when the membrane is disposed on the membrane frame 744). In other embodiments, however, a first gasket can have another suitable shape for sealing a first portion of a pumping chamber configured to receive oxygen from a pneumatic system.

The first gasket 742 can be constructed of any suitable material. In some embodiments, for example, the first gasket 742 is constructed of silicone, an elastomer, or the like. The first gasket 742 can have any suitable thickness. For example, in some embodiments, the first gasket 742 has a thickness within a range of about 0.1 inches to about 0.15 inches. More specifically, in some embodiments, the first gasket 742 has a thickness of about 0.139 inches. The first gasket 742 can have any suitable level of compression configured to maintain the seal about the first portion 727 of the pumping chamber 725 when the components of the lid assembly 710 are assembled. For example, in some embodiments, the first gasket 742 is configured to be compressed by about 20 percent.

The membrane 740 is configured to permit diffusion of gas (e.g., oxygen) from the first portion 727 of the pumping chamber 725 through the membrane to the second portion 729 of the pumping chamber, and vice versa. The membrane 740 is configured to substantially prevent a liquid (e.g., the perfusate) from passing through the membrane. In this manner, the membrane 740 can be characterized as being semipermeable. The membrane frame 744 is configured to support the membrane 740 (e.g., during the oxygenation of the perfusate and perfusion of the bodily tissue). The membrane frame 744 can have a substantially round or circular shaped perimeter.

As illustrated in FIG. 11, the membrane 740 is disposed within the pumping chamber 725 at an angle with respect to a horizontal axis A4. In this manner, the membrane 740 is configured to facilitate movement of fluid towards a purge port 706 in fluid communication with the pumping chamber 725, as described in more detail herein. The angle of incline of the membrane 740 can be of any suitable value to allow fluid (e.g., gas bubbles, excess liquid) to flow towards the purge port 706 and exit the pumping chamber 725. In some embodiments, the angle of incline is approximately in the range of 1°-10°, in the range of 2°-6°, in the range of 2.5°-5°, in the range of 4°-5° or any angle of incline in the range of 1°-10° (e.g., approximately 1°, 2°, 3°, 4°, 5°, 6°, 7°, 8°, 9°, 10°). More specifically, in some embodiments, the angle of incline is approximately 5°.

The membrane 740 can be of any suitable size and/or thickness, including, for example, a size and/or thickness described with respect to another membrane herein (e.g., membrane 40 or 140). The membrane 740 can be constructed of any suitable material. For example, in some embodiments, the membrane is constructed of silicone, plastic, or another suitable material. In some embodiments, the membrane is flexible. In this manner, the membrane 740 is configured to be more resistant to being torn or otherwise damaged in the presence of a flexural stress caused by a change in pressure in the pumping chamber due to the inflow and/or release of oxygen or another gas.

Referring to FIG. 11, the lid 720 includes the purge port 706 disposed at the highest portion of the pumping chamber 725 (e.g., at the highest portion or point of the second portion 729 of the pumping chamber 725). The purge port 706 is configured to permit movement of fluid from the pumping chamber 725 to an area external to the apparatus 700. The purge port 706 can be similar in many respects to a purge port described herein (e.g., port 78, purge ports 106, 306).

As noted above, the upper surface 734 of the base 732 forms the bottom portion of the pumping chamber 725. A lower surface 736 of the base 732 forms an upper portion of an organ chamber 792. The organ chamber 792 is formed by the canister 790 and the lower surface 736 of the base 732 when the lid assembly 710 is coupled to the canister 790. A well 758 is extended from the lower surface 736 of the base 732 (e.g., into the organ chamber 792). The well 758 is configured to contain a sensor (not shown) configured to detect the temperature within the organ chamber 792. The well 758 can be configured to substantially fluidically isolate the sensor from the organ chamber 792, thereby preventing liquid (e.g., perfusate) from the organ chamber from engaging the sensor directly. In some embodiments, the sensor contained in the well 758 can be in electrical communication with a control unit (such as control unit 500, described in detail above).

The base 732 is coupled to the lid 720. In some embodiments, the base 732 and the lower portion 723 of the lid 720 are coupled together, e.g., about a perimeter of the pumping chamber 725. The base 732 and the lid 720 can be coupled using any suitable mechanism for coupling including, but not limited to, a plurality of screws, an adhesive, a glue, a weld, another suitable coupling mechanism, or any combination of the foregoing. A gasket 748 is disposed between the base 732 and the lid 720. The gasket 748 is configured to seal an engagement of the base 732 and the lid 720 to substantially prevent fluid in the pumping chamber 725 from leaking therebetween. In some embodiments, the gasket 748 is an O-ring. The gasket 748 can be similar in many respects to a gasket described herein (e.g., gasket 148, 742).

The base 732 defines a lumen 735 configured to be in fluid communication with a lumen 774 of an organ adapter 770. The base 732 is configured to permit oxygenated perfusate to move from the pumping chamber 725 through its lumen 735 into the lumen 774 of the organ adapter 770 towards the organ chamber 792. In this manner, the lumen 735 of the base 732 is configured to help fluidically couple the pumping chamber 725 and the organ chamber 792. As shown in FIG. 11, the path of the perfusate may be through the organ. The organ adapter 770 is configured to substantially retain the bodily tissue with respect to the apparatus 700. The organ adapter 770 can be similar in many respects to an adapter described herein (e.g., adapter 26, organ adapter 170).

Referring to FIG. 11, the lid assembly 710 includes a fill port 708 configured to permit introduction of a fluid (e.g., the perfusate) into the organ chamber 792 (e.g., when the lid assembly 710 is coupled to the canister 790). The fill port 708 can be similar in many respects to a port described herein (e.g., port 74, fill port 108). In the embodiment illustrated in FIG. 11, the fill port 708 includes a fitting 707 coupled to the lid 720 and defines a lumen 709 in fluidic communication with a lumen 737 defined by the base 732, which lumen 737 is in fluidic communication with the organ chamber 792. The fitting 707 can be any suitable fitting, including, but not limited to, a luer lock fitting. The fill port 708 can include a cap 705 removeably coupled to the port. The cap 705 can help prevent inadvertent movement of fluid, contaminants, or the like through the fill port 708.

The lid assembly 710 is configured to be coupled to the canister 790. The lid assembly 710 includes handles 712, 713. The handles 712, 713 (FIG. 10) are each configured to facilitate coupling the lid assembly 710 to the canister 790, as described in more detail herein. Said another way, the handles 712, 713 are configured to move between a closed configuration in which the handles prevent the lid assembly 710 being uncoupled or otherwise removed from the canister 790, and an open configuration in which the handles do not prevent the lid assembly 710 from being uncoupled or otherwise removed from the canister. The handles 712, 713 are moveably coupled to the lid 720. Each handle 712, 713 can be pivotally coupled to opposing sides of the coupling mechanism 850 (described in more detail herein) disposed about the lid 720. For example, each handle 712, 713 can be coupled to the coupling mechanism 850 via an axle (not shown).

The canister 790 can be configured to enable an operator of the apparatus 700 to view the bodily tissue when the bodily tissue is sealed within the organ chamber 792. In some embodiments, for example, at least a portion of the canister 790 (e.g., the wall 791) is constructed of a clear or transparent material. In another example, in some embodiments, at least a portion of the canister 790 (e.g., the wall 791) is constructed of a translucent material. In yet another example, in some embodiments, a canister includes a window through which at least a portion of the organ chamber can be viewed.

As noted above, the apparatus 700 is configured for controlled delivery of fluid (e.g., oxygen) from an external source (not shown) into the pumping chamber 725 of the lid assembly 710. The external source can be, for example, an oxygen cylinder. In some embodiments, the apparatus 700 includes the pneumatic system, such as pneumatic system 200, configured for controlled venting of fluid (e.g., carbon dioxide) from the pumping chamber 725 to an area external to the apparatus 700 (e.g., to the atmosphere). The pneumatic system 200 is moveable between a first configuration in which the pneumatic system is delivering fluid to the pumping chamber 725 and a second configuration in which the pneumatic system is venting fluid from the pumping chamber 725. The pneumatic system 200 is described in detail above with respect to apparatus 100.

In use, the bodily tissue is coupled to at least one of the organ adapter 770 or tubing configured to be coupled to the organ adapter. The organ adapter 770 can be coupled to the lid assembly 710. Optionally, a desired amount of perfusate can be disposed within the compartment 794 of the canister 790 prior to disposing the lid assembly 710 on the canister. For example, in some embodiments, a perfusate line (not shown) is connected to the organ adapter 770 and the organ is flushed with perfusate, thereby checking for leaks and partially filling the canister 790 with perfusate. Optionally, when the canister 790 is substantially filled, the perfusate line can be disconnected. The lid assembly 710 is disposed on the canister 790 such that the bodily tissue is received in the organ chamber 792. The lid assembly 710 is coupled to the canister 790. Optionally, the lid assembly 710 and the canister 790 are coupled via the retainer ring 850. Optionally, a desired amount of perfusate is delivered to the organ chamber 792 via the fill port 708.

A desired control scheme of the pneumatic system 200 is selected. Oxygen is introduced into the first portion 727 of the pumping chamber 725 via the pneumatic system 200 based on the selected control scheme. The pneumatic system 200 is configured to generate a positive pressure by the introduction of oxygen into the first portion 727 of the pumping chamber 725. The positive pressure helps to facilitate diffusion of the oxygen through the membrane 740. The oxygen is diffused through the membrane 740 into the perfusate disposed in the second portion 729 of the pumping chamber 725, thereby oxygenating the perfusate. Because the oxygen will expand to fill the first portion 727 of the pumping chamber 725, substantially all of an upper surface 741 of the membrane 740 which faces the first portion of the pumping chamber can be used to diffuse the oxygen from the first portion into the second portion 729 of the pumping chamber.

As the organ uses the oxygen, the organ will release carbon dioxide into the perfusate. Such carbon dioxide can be diffused from the second portion 729 of the pumping chamber 725 into the first portion 727 of the pumping chamber 725. Carbon dioxide within the first portion 727 of the pumping chamber is vented via a control line (not shown) to a valve (not shown), and from the valve through a vent line (not shown) to the atmosphere external to the apparatus 700.

The positive pressure also causes the membrane 740 to flex, which transfers the positive pressure in the form of a pulse wave into the oxygenated perfusate. The pulse wave generated by the pumping chamber is configured to facilitate movement of the oxygenated perfusate from the second portion 729 of the pumping chamber 725 into the bodily tissue via the organ adapter 770 (and any intervening structure or tubing), thus perfusing the bodily tissue. In some embodiments, the pumping chamber 725 is configured to generate a pulse wave in a similar manner as pumping chamber, described in detail above with respect to apparatus 100.

At least a portion of the perfusate perfused through the organ is received in the organ chamber 792. In some embodiments, the pulse wave is configured to flow through the perfusate disposed in the organ chamber 792 towards the floor 793 of the canister 790. The floor 793 of the canister 790 is configured to flex when engaged by the pulse wave. The floor 793 of the canister 790 is configured to return the pulse wave through the perfusate towards the top of the organ chamber 792 as the floor 793 of the canister 790 is returned towards its original non-flexed position. In some embodiments, the returned pulse wave is configured to generate a sufficient pressure to open the valves 738A, 738B disposed at the highest positions in the organ chamber 792. In this manner, the returned pulse wave helps to move the valves 738A, 738B to their respective open configurations such that excess fluid (e.g., carbon dioxide released from the bodily tissue and/or the perfusate) can move through the valves from the organ chamber 792 to the pumping chamber 725. The foregoing perfusion cycle can be repeated as desired, including in any manner described above with respect to other apparatus described herein (e.g., apparatus 10, 100, 300).

Although the perfusion cycle has been described herein as including a substantially regular intermittent pulse of oxygen from the pneumatic system 200 to the pumping chamber 725, in other embodiments, the pneumatic system 200 can be configured to deliver oxygen to the pumping chamber 725 at a different interval (e.g., flow interval), such as those variations described above with respect to apparatus 100 and pneumatic system 200.

Although the lid assembly 710 has been illustrated and described as being configured for use with the canister 790, in other embodiments, the lid assembly 710 can be configured for use with canisters having different configurations. For example, although the canister 790 has been illustrated and described herein as being of a certain size and/or shape, in other embodiments, a canister having any suitable dimensions can be configured for use with the lid assembly 710. In some embodiments, for example, a first canister configured for use with the lid assembly 710 is dimensionally configured to accommodate a first type of bodily tissue, and a second canister configured for use with the lid assembly 710 is dimensionally configured to accommodate a second type of bodily tissue different than the first type of bodily tissue. For example, the canister 790 illustrated in FIG. 12 and described herein with respect to apparatus 700 can be dimensioned to accommodate an organ, such as a heart. The canister 790 can be, for example, a 2.7 liter cylindrical canister having a height greater than or substantially equal to a width of the floor 793. For example, as shown in FIG. 12, the compartment 794 of the canister 790 can have a height Hi of about 15 cm (or about 5.91 inches) and a diameter $D_i$ of about 15 cm (note that diameter $D_i$ of the compartment 794 can be different from a diameter D3 of the top rim 795 of the canister 790, which can be about 20 cm (or about 7.87 inches)). Accordingly, when the canister 790 is coupled to the lid assembly 710, the apparatus 700 can have an overall diameter of about 24 cm (or about 9.44 inches) and an overall height of about 22.3 cm (or about 8.77 inches).

In another embodiment, as illustrated in FIG. 13, a differently dimensioned canister 990 can be used with the lid assembly 710. The canister 990 can be dimensioned to accommodate the second bodily tissue, such as a kidney. The canister 990 can be, for example, a 3.0 liter cylindrical canister having a wall 991 height less than a width of a floor 993 of the canister. For example, as shown in FIG. 13, the compartment 994 of the canister 990 can have a height 112 less than the height Hi of canister 790 and a diameter D2 greater than or equal to the diameter Di of canister 790. The height H2 and diameter D2 of the compartment 994 can be such that the lid assembly 710 coupled to the canister 990 via the retainer ring 850 collectively have an overall height of about 16.5 cm (or about 6.48 inches) and a diameter of about 24 cm (or about 9.44 inches). It should be noted that although specific dimensions are described herein, in other embodiments, such dimensions can be different and still be within the scope of the invention. The thickness of the floor 993 of the canister 990 can be selected based on the height and width dimensions of the canister 990 to ensure that the floor 993 is configured to properly flex in the presence of the pulse wave, as described above, and may be the same as or different than the thickness of the floor 793 of canister 790. The canister 990 includes a plurality of segments 997 protruding from an outer surface of the wall adjacent an upper rim 995 of the canister 990. The plurality of segments 997 are configured to facilitate coupling the canister 990 to the lid assembly 710 and the retainer ring 850, as described above with respect to the canister 790.

Referring to FIG. 14, in some embodiments, an apparatus includes a basket 870 configured to be disposed in a compartment 994 of the canister 990. The basket 870 is configured to support the bodily tissue (e.g., kidney K) within the compartment 994. In some embodiments, for example, the basket 870 includes a bottom portion 872 on which the bodily tissue can be disposed. In some embodiments, the bottom portion 872 of the basket 870 is smooth. The bottom portion 872 can be slightly curved to accommodate curvature of the bodily tissue. In some embodiments, netting (not shown) can be used to retain the bodily tissue with respect to the basket 870 (e.g., when the bodily tissue is disposed on the bottom portion 872 of the basket 870). Arms 874A, 874B are disposed on a first side of the bottom portion 872 of the basket 870 opposite arms 876A, 876B disposed on a second side of the bottom portion of the basket. Each pair of arms 874A, 874B and 876A, 876B is extended vertically and terminates in a handle portion 875, 877, respectively, that couples the upper end portions of the arms.

In some embodiments, as shown in FIG. 14, a shape of the outer perimeter of the bottom portion 872 of the basket 870 can substantially correspond to a shape of a perimeter of the canister 990, such that outer edges of lower end portions of the arms 874A, 874B, 876A, 876B each abut an inner surface of the wall 991 of the canister. In this manner, lateral movement of the basket 871, and thus of the organ supported thereon, is prevented, or at least restricted. The handle portions 875, 877 can be configured to engage the lower surface 736 of the base 732 of the lid assembly 710 when the basket 870 is received in the canister's 990 compartment 994 and the canister is coupled to the lid assembly 710. In this manner, vertical movement of the basket 870 with respect to the canister 990 is prevented.

While various embodiments have been described above, it should be understood that they have been presented by way of example only, and not limitation. Where methods described above indicate certain events occurring in certain order, the ordering of certain events may be modified. For example, selecting the control scheme of the pneumatic system 200 can occur before the coupling the bodily tissue to the organ adapter 170, 770. Additionally, certain of the events may be performed concurrently in a parallel process when possible, as well as performed sequentially as described above. Furthermore, although methods are described above as including certain events, any events disclosed with respect to one method may be performed in a different method according to the invention. Thus, the breadth and scope should not be limited by any of the above-described embodiments.

While the invention has been particularly shown and described with reference to specific embodiments thereof, it will be understood that various changes in form and details may be made. For example, although the valves disposed at the highest portion of the organ chamber have been illustrated and described herein as being a ball check valve, in other embodiments, a different type of valve configured to permit unidirectional flow of a fluid from the organ chamber into the pumping chamber can be included in the apparatus. For example, in some embodiments, an apparatus includes a different type of a check valve, such as a diaphragm check valve, a swing check valve, a life check valve, or the like. In another example, in some embodiments, an apparatus includes a valve that is different than a check valve.

Although the valve 210 of the pneumatic system 200 has been illustrated and described herein as being a solenoid valve, in other embodiments, the pneumatic system can include a different type of valve configured to control the flow of oxygen into the pumping chamber.

Although the valve 210 of the pneumatic system 200 has been illustrated and described herein as including three ports, in other embodiments, a valve of a pneumatic system can include a different number of ports. For example, in some embodiments, the valve includes one, two, four, or more ports.

Although the pneumatic systems (e.g., pneumatic system 200, 220) have been illustrated and described as including a specific number of control orifices (e.g., one control orifice 207 and two control orifices 223, 225, respectively), in other embodiments, a pneumatic system can include any suitable number of control orifices. For example, a pneumatic system can include one, two, three, four, or more control orifices.

EXAMPLES

Example 1

Oxygen Consumption in Hypothermically Perfused Rat Kidneys

Adult Sprauge-Dawley albino rats weighing between 350 to 500 grams were anesthetized by intravenous injection with 25 ml/kg of sodium pentobarbital. Rodents were intubated and ventilated with 40% oxygen to maintain normal arterial blood oxygenation. In the supine position kidneys were exposed via a midline incision in the lower abdominal cavity. The rodent was heparinized, followed by the insertion of a catheter into the descending aorta above the kidneys. A second catheter was inserted into the inferior vena cava just below the kidneys. Following cross clamping of the aorta and inferior vena cava above and below the catheters, an infusion of cold University of Wisconsin Solution (UWS) at 4° C. was initiated. Infusion was terminated after all blood was cleared from the isolated organs. Cold saline (4° C.) was poured over the kidneys during infusion and removed by suction. The aorta and inferior vena cava were ligated at the cross clamp then cut, as were the ureters. The kidneys were quickly dissected free and placed on ice for catheterization of the renal arteries, veins and ureters.

Figure 15:
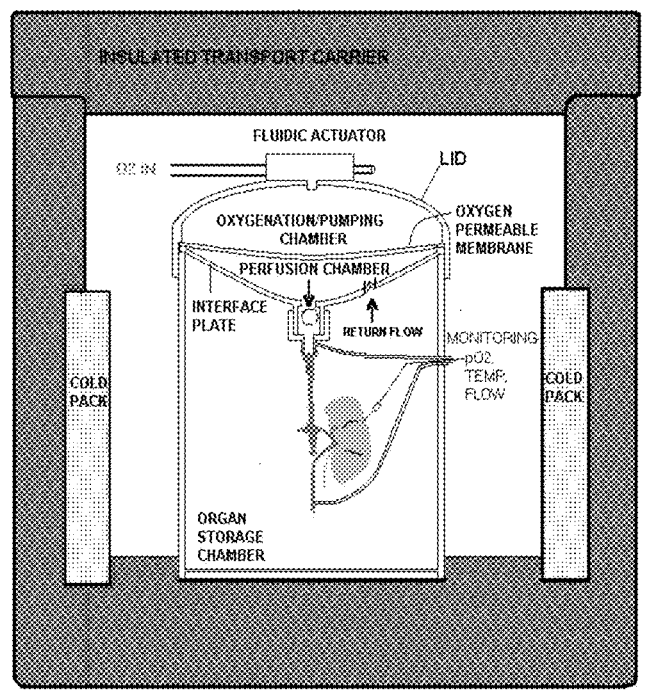
FIG. 15 is a diagram of a laboratory perfusion chamber for oxygenated perfusion of a rodent kidney.

Each kidney (n=8) was attached to the organ preservation device shown in FIG. 15 via a renal arterial cannula and immersed into cold (4° C.) freshly prepared University of Wisconsin Solution. The renal venous catheter was attached to a two way port which could be switched so that the outflow perfusate from the kidney could be collected either externally or re-circulated back to the organ storage chamber. Perfusion was initiated at 70 pulses/min. The preservation device was placed into a Styrofoam case into which 3 cold packs had been previously placed. During the subsequent 24 hour preservation period, temperature, renal arterial and venous pressures were monitored continuously. Samples of the preservation solution flowing into and out of the organs were taken at 60 minute intervals for oxygen partial pressure measurements.

The renal perfusion rate was measured by collecting renal venous outflow from each kidney for 15 seconds and calculating the flow/minute. Renal vascular resistance (RVR) was calculated by dividing the mean perfusion pressure by the renal vein outflow in ml/min. The oxygen consumption rate (OCR) was calculated by; (1) multiplying the difference between the $pO_2$ of the delivered UWS and the $pO_2$ of the organ outflow by 0.00006 the oxygen solubility factor per ml of solution at 4° C., (2) multiplying the result by the organ perfusion in ml/min, (3) normalizing this result by the weight of the organ. That is, using the methods described in the detailed description with a value of a=0.00006.

During the course of the experiment, the partial oxygen pressure of the preservation solution (UWS) entering the kidneys during hypothermic mechanical perfusion (HMP) was steadily increased from approximately 150 mmHg to approximately 360 mmHg. The $pO_2$ of the perfusate exiting the organs, on average, rose to 291±117 mmHg during the 24 hour perfusion period. The difference in the partial pressure of oxygen, before and after the kidney was relatively constant throughout the perfusion period, and averaged 70.3±30.2 mmHg. The results of the experiment, including kidney weight, temperature, perfusion pressure, perfusate flow, oxygen consumption and vascular resistance during HMP are summarized in Table 1.

TABLE 1

Average preservation data for HMP rodent kidneys (n = 8)

| | |
|---|---|
| Kidney Weight (g) | 8.2 ± 1.1 |
| Temp (° C.) | 7.3 ± 0.7 |
| Perfusion Pressure (mmHg) | 10.1 ± 3.6 |
| UWS Flow (ml/min) | 4.9 ± 0.4 |
| OCR (mlO$_2$/min/g) | 0.0025 ± 0.0009 |
| RVR (mHg/ml/min/g) | 0.250 ± 0.077 |

Although not shown, the OCR value for each kidney was relatively constant throughout the 24 hour period and the overall range of OCR values between the 8 kidneys was small. This data suggests that OCR would be a good indicator of organ health.

Example 2

Figure 16:
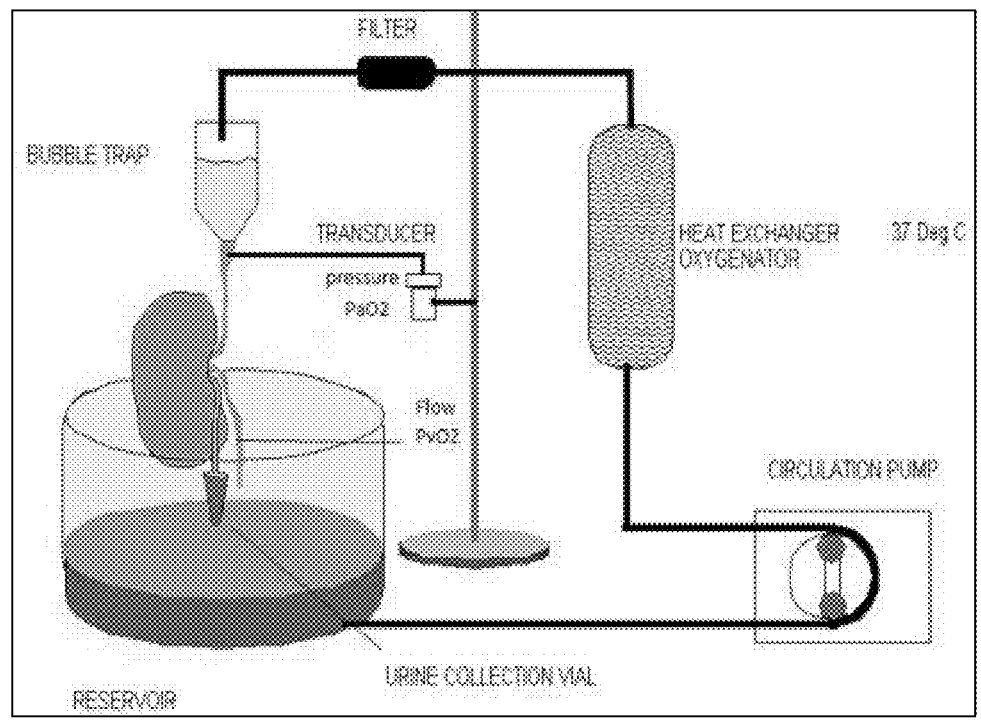
FIG. 16 is a diagram of a laboratory setup for measuring glomerular flow rates from a rodent kidney.

Correlation Between Glomerular Flow Rates and Oxygen Consumption in Rat Kidneys Following the HMP period described in Example 1, each kidney was removed from the preservation device and connected to a Langendorff device via the renal artery catheter, as shown in FIG. 16. While on this device, the rodent organs were perfused with warm (37° C.) oxygenated (100% $O_2$) Krebs-Haenseleit (K-H) solution containing inulin (15 mg/100 ml). Perfusion was initiated slowly and increased at 5 minute intervals until a mean arterial pressure of 100 mmHg was achieved. Urine, arterial and venous samples were collected from each kidney at 7, 30, 60, and 90, 120, and 150 minutes for inulin clearance and urine output measurement. The partial pressure of oxygen in the K-H solution entering the renal arteries and exiting the renal veins was measured on a blood gas machine (TruPoint Irma™). Organ perfusion was measured by collecting the outflow from the renal veins during a 15 second time interval and adjusting to flow/minute. Oxygen consumption rate was calculated as above, but using a=0.00003, because of the temperature change (37° C.). RVR was also calculated as described above. The glomerular filtration rate (GFR) was calculated by multiplying the inulin concentration in the urine (mg/ml) by the urine flow (ml/min) and dividing by the inulin concentration in the plasma (mg/ml).

All kidneys, which were previously hypothermic, reached stable GFR within 30 minutes of rewarming following attachment to the Langendorff device (FIG. 16). During functional testing on the Langendorff, the partial pressure of oxygen in the K-H solution entering the renal artery was 392±78 mmHg, and the partial pressure of oxygen exiting the renal vein was 272.0±81.0 mmHg. The oxygen partial pressure differential was stable during the 180 min of testing, with an average value of 120.0±34.1 mmHg. (Notably higher than the average of 70.3±30.2 mmHg, at 7° C., above.) Kidney weight, temperature, perfusion pressure, perfusate flow, oxygen consumption vascular resistance and GFR during Langendorff testing are summarized in Table 2.

TABLE 2

Average organ function measurements during perfusion in the isolated organ preparation (n = 8).

| | |
|---|---|
| Kidney Weight(g) | 8.2 ± 1.1 |
| Temperature(° C.) | 37.0 |
| Perfusion Pressure (mmHg) | 100 |
| Krebs-Haenseleit Flow (ml/min) | 31.9 ± 4.9 |
| OCR(mlO$_2$/min/g) | 0.015 ± 0.006 |

TABLE 2-continued

Average organ function measurements during perfusion
in the isolated organ preparation (n = 8).

| | |
|---|---|
| RVR(mmHg/ml/min/g) | 0.397 ± 0.111 |
| GFR ml/min/g. | 0.057 ± 0.037 |

Figure 17:
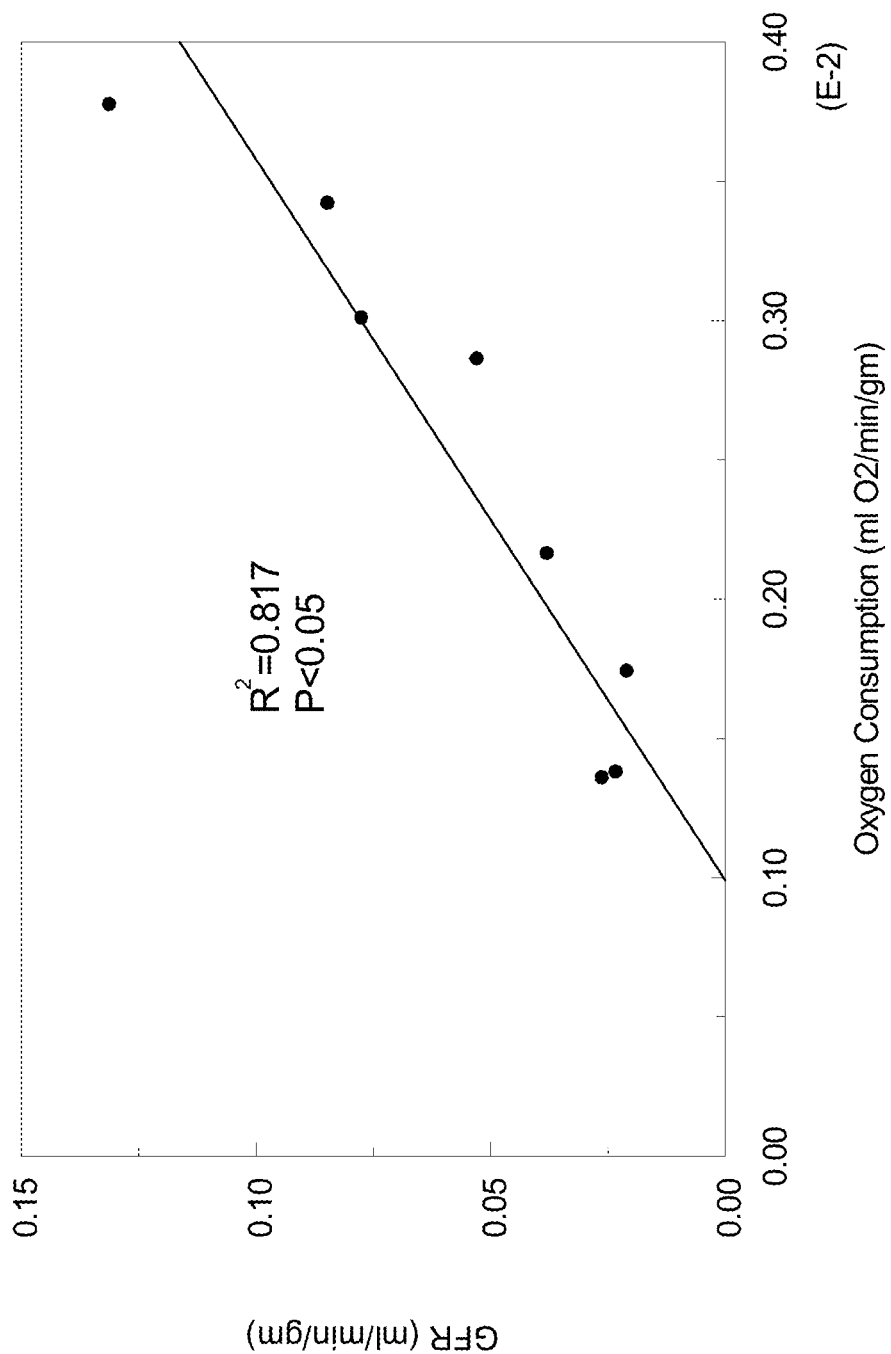
FIG. 17 shows a measured correlation between measured oxygen consumption and glomerular flow rate.

A linear regression model was applied to the RVR during oxygenated perfusion preservation and post-preservation organ function as determined by GFR measured on the Langendorff device, however the results showed that the correlation was poor ($r^2=0.258$ p=0.199). In contrast, the correlation between oxygen consumption by the kidneys and GFR was good. In particular, oxygen consumption during oxygenated HMP (Example 1) was significantly correlated ($r^2=0.871$ p<0.05) to post-preservation GFR, as shown in FIG. 17. Thus, the measurement of organ oxygen consumption during oxygenated HMP appears to have significant value in predicting post-preservation organ function as indicated by GFR. This example suggests that oxygen consumption rate is a better predictive model of organ viability than RVR.

Example 3

Oxygen Consumption in DCD Model Kidneys Undergoing Hypothermic Perfusion

Kidneys were recovered through a midline abdominal incision from 20 to 25 kg Nubian goats (n=5) after 60 minutes of warm ischemia following pentobarbital euthanasia. (Because the kidneys were left in the animals 60 minutes post-mortem, they are relevant to donation after cardiac death (DCD) kidneys, i.e., where the kidneys are not immediately harvested upon death of the donor.) The renal arteries and veins of the kidneys were cut at the aorta, and inferior vena cava respectively. The renal artery and vein of each kidney were cannulated. Cold (4° C.) Krebs-Haenselite (KH) solution, containing 20 units of Heparin per liter, was flushed via gravity through the renal artery until no blood was visible exiting the renal vein. Once cleared, each kidney was weighed and then attached to a perfusion device of the invention, e.g., as described above (PARAGONIX SHERPA™, Paragonix Technologies, Cambridge, Mass.) via a renal artery connector. The kidney was then submerged into the organ storage canister previously filled with cold 4° C. KH solution. Sampling catheters from the renal artery and vein were exteriorized for measurement of inflow and outflow oxygen partial pressure as described in EXAMPLE 1 (see FIG. 15). The catheters were also used for measurement of arterial and venous pressures. The perfusion device was placed within a styrofoam storage chest and maintained at 4° C. with cold packs.

The kidneys were then perfused with hypothermic oxygenate KH solution for 24 hours while flow rate, flow pressure, and oxygen consumption were monitored. The kidneys were perfused at a flow rate between 0.1 and 0.3 ml g$^{-1}$ min$^{-1}$ at 70 pulses min$^{-1}$ for 24 hours. Organs were perfused by a mean flow of 16.8±3.0 ml/min (0.30±0.02 ml/min/g) and were maintained at a temperature of 5.4±0.3° C. during the perfusion period.

Perfusate flow and pressure in the renal artery were measured continuously during the perfusion. Venous pressure was also measured continuously at the renal vein. Perfusion pressure was calculated as the difference between the mean renal artery pressure and the mean renal vein pressure. Mean perfusion pressure was 8.3±3.0 mmHg.

Figure 18:
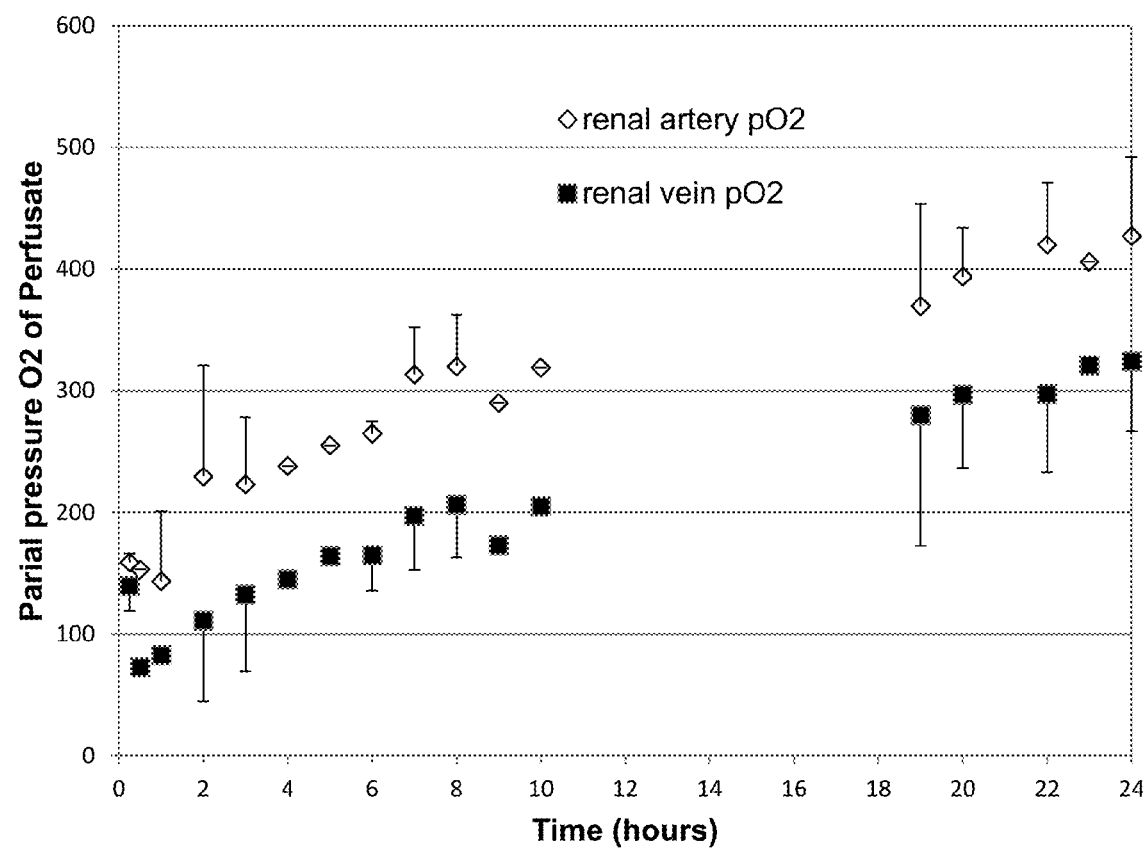
FIG. 18 shows $O_2$ partial pressure measurements from arterial and venous perfusate flows in a DCD (donation after cardiac death) kidney model undergoing hypothermic perfusion.

In addition to perfusate flow and pressure, oxygen consumption was measured at the beginning and the end of the perfusion period, as shown in FIG. 18. The consumption was equivalent to the difference between $O_2$ partial pressure of the perfusate entering the renal artery and exiting the renal vein. The partial pressure of oxygen in the perfusate delivered to the kidneys at the start of perfusion was 150 mmHg, then rose to 427±65 mmHg by 24 hours. (See FIG. 18) Oxygen delivery to the organ was 0.269 mlO$_2$/min/100 g at the start of perfusion and increased to 0.771 mlO$_2$/min/100 g by 24 hours. The A-V pO$_2$ difference was constant during the entire perfusion period at 96.8±29.9 mmHg. Fifteen minutes following the start of perfusion, oxygen consumption was 0.05±0.04 mlO$_2$/min/100 g. After 2 hours of perfusion the mean oxygen consumption rose to 0.16±0.04 mlO$_2$/min/100 g and remained approximately constant for the rest of the perfusion period. (See FIG. 18)

The data show that physiologic function of a kidney that has experienced 60 minutes of warm ischemia improves (as indicated by oxygen consumption rate) after a few hours of hypothermic oxygenated perfusion. Additionally, the data suggest that the function can be maintained for some time (i.e., greater than 24 hours) by providing continued hypothermic oxygenated perfusion.

The data suggest that organs recovered from DCD donors, which often experience substantial periods of warm ischemia, may recover to viability using hypothermic oxygenated perfusion, e.g., using a device of the invention, e.g., PARAGONIX SHERPA™. Additionally, the data suggest that viable DCD organs may be maintained for at least 24 hours, which would afford sufficient time to match the donor organ to a recipient and transport the organ to the recipient.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A method for evaluating the suitability of an organ for transplant, the method comprising:
   inserting an organ into a mobile perfusion machine comprising:
      a preservation solution; and
      a pneumatic system configured to oxygenate the preservation solution to create an oxygenated solution, and further configured to vary a pressure of the oxygenated solution at least once per minute to create a differential perfusion pressure;
   perfusing the organ with the oxygenated solution at a hypothermic temperature;
   measuring the oxygen consumption rate of the organ;

comparing the measured oxygen consumption rate to a functional oxygen consumption rate wherein a measured oxygen consumption rate greater than or equal to the functional oxygen consumption rate is indicative of a suitable organ; and using a processor to alter a perfusion property based on the comparison.

2. The method of claim 1, wherein the differential perfusion pressure is greater than 0 mm Hg and less than or equal to 120 mm Hg.

3. The method of claim 2, wherein the differential perfusion pressure is greater than 0 mm Hg and less than or equal to 50 mm Hg.

4. The method of claim 1, wherein the functional oxygen consumption rate is greater than or equal to 50 nmolO$_2$/min/g of organ mass.

5. The method of claim 1, wherein the organ is selected from the group consisting of heart, kidney, liver, lung, and pancreas.

6. The method of claim 1, wherein the organ is perfused at a temperature of less than 10° C.

7. The method of claim 1, wherein the organ is from an expanded criteria donor (ECD) or from a donation after cardiac death (DCD).

8. The method of claim 1, additionally comprising monitoring vascular resistance of the organ to perfusion.

9. The method of claim 1, wherein the mobile perfusion machine varies the pressure on the oxygenated solution at least once every 10 seconds.

10. The method of claim 1, wherein the mobile perfusion machine additionally comprises one or more oxygen sensors.

11. The method of claim 1, wherein the mobile perfusion machine oxygenates the preservation solution with a partial pressure of oxygen of at least 100 mmHg (100 Torr).

12. The method of claim 11, wherein the mobile perfusion machine displays a value indicative of the oxygen consumption rate of the organ.

13. The method of claim 1, wherein the perfusion property is one selected from the list consisting of: perfusion temperature, flow rate, and pressure.

* * * * *